(12) United States Patent
Cheresh et al.

(10) Patent No.: US 7,803,399 B2
(45) Date of Patent: Sep. 28, 2010

(54) DELIVERY SYSTEM FOR NUCLEIC ACIDS

(75) Inventors: David A. Cheresh, Encinitas, CA (US);
John Hood, San Diego, CA (US); Mark Bednarski, Los Altos, CA (US)

(73) Assignees: The Scripps Research Institute, La Jolla, CA (US); Board of Trustees of the Leland Stanford, Jr., University, Palo Alto, CA (US)

(*) Notice: Subject to any disclaimer, the term of this patent is extended or adjusted under 35 U.S.C. 154(b) by 1100 days.

(21) Appl. No.: 11/396,743

(22) Filed: Apr. 3, 2006

(65) Prior Publication Data

US 2006/0188560 A1    Aug. 24, 2006

Related U.S. Application Data

(62) Division of application No. 10/158,761, filed on May 30, 2002, now Pat. No. 7,025,987.

(60) Provisional application No. 60/345,891, filed on Oct. 29, 2001, provisional application No. 60/294,309, filed on May 30, 2001.

(51) Int. Cl.
*A61K 9/127*     (2006.01)
*A61K 31/70*    (2006.01)
*C12N 15/00*    (2006.01)
*C12N 15/88*    (2006.01)

(52) U.S. Cl. .................. 424/450; 514/44; 435/455; 435/458

(58) Field of Classification Search ............... None
See application file for complete search history.

(56) References Cited

U.S. PATENT DOCUMENTS

| 6,458,026 | B1 * | 10/2002 | Hart ............... 435/69.1 |
| 6,521,211 | B1 * | 2/2003 | Unger et al. ........ 424/9.52 |
| 2002/0172711 | A1 * | 11/2002 | Martin et al. ......... 424/450 |
| 2003/0203865 | A1 * | 10/2003 | Harvie et al. .......... 514/44 |

FOREIGN PATENT DOCUMENTS

WO    WO0026212 A1 *  5/2000

* cited by examiner

*Primary Examiner*—Janet Epps-Smith
(74) *Attorney, Agent, or Firm*—Olson & Cepuritis, Ltd.

(57) ABSTRACT

$\alpha_v\beta_3$ Integrin receptor targeting liposomes comprise a cationic amphiphile such as a cationic lipid, a neutral lipid, and a targeting lipid. The targeting lipid includes a non-peptidic $\alpha_v\beta_3$ integrin antagonist.

7 Claims, 18 Drawing Sheets

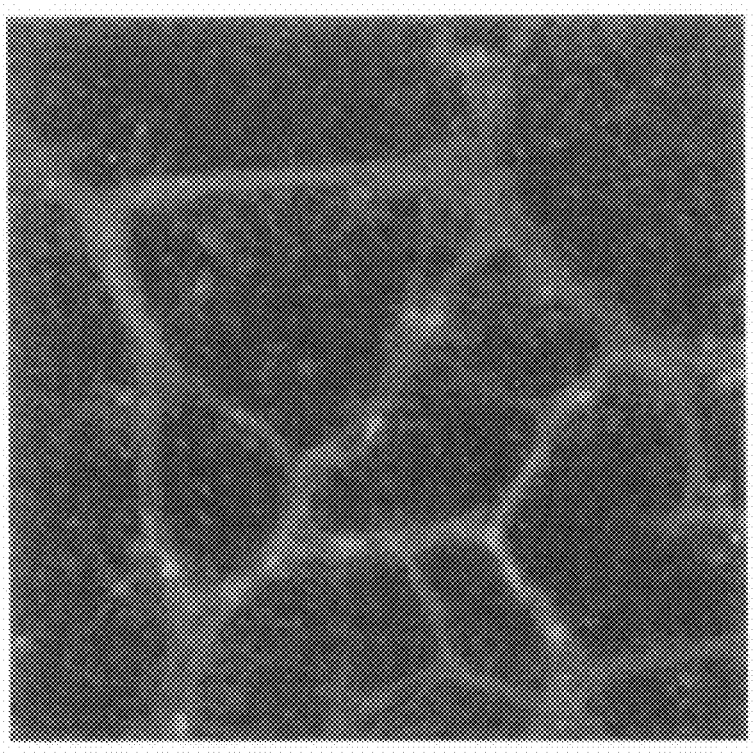
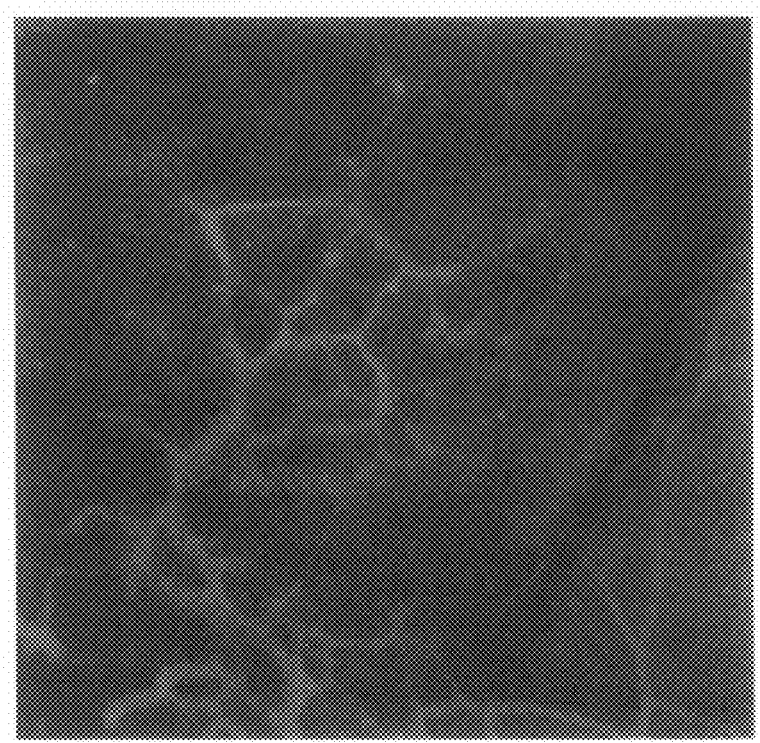
Targeted gene delivery to Angiogenic vessels of the Eye
FIG. 15B
FIG. 15A

DELIVERY SYSTEM FOR NUCLEIC ACIDS

CROSS-REFERENCE TO RELATED APPLICATIONS

This is a divisional application of U.S. patent application Ser. No. 10/158,761, filed on May 30, 2002, now U.S. Pat. No. 7,025,987, which claims the benefit of U.S. Provisional Applications for Patent No. 60/345,891 filed on Oct. 29, 2001, and No. 60/294,309 filed on May 30, 2001, the disclosures of which are incorporated herein by reference.

GOVERNMENTAL RIGHTS

A portion of the work described herein was supported by grant numbers CA 50286, CA 86312, CA 45726, CA 52086, and CA 78045 from the National Institutes of Health. The United States Government has certain rights in this invention.

FIELD OF THE INVENTION

This invention relates to the delivery of genes and like nucleic acids to targeted sites in vivo. More particularly, this invention relates to liposome-mediated delivery of genes to angiogenic blood vessels.

BACKGROUND OF THE INVENTION

Integrins are a class of cellular receptors known to bind extracellular matrix proteins, and therefore mediate cell-cell and cell-extracellular matrix interactions, generally referred to as cell adhesion events. Although many integrins and the ligands that bind an integrin are described in the literature, the biological function of many of the integrins remains elusive. The integrin receptors constitute a family of proteins with shared structural characteristics of noncovalent heterodimeric glycoprotein complexes formed of α and β subunits, Cheresh & Mecham, eds., *Integrins: Molecular and Biological Responses to the Extracellular Matrix*, Academic Press, Inc., San Diego, Calif. 92101 (1994), Horton, *Int. J. Exp. Pathol.*, 71:741-759 (1990). The specific cell adhesion roles that these integrins play in the many cellular interactions in tissues are still under investigation.

Endothelial-matrix interactions play a role during angiogenesis, the formation of new blood vessels. A cell adhesion receptor known as $\alpha_v\beta_3$ integrin is found on the surface of activated endothelial cells that participate in angiogenesis.

It is well known that angiogenesis is also a requirement for malignant tumor growth and metastasis. In the absence of angiogenesis local tumor expansion is suppressed. Also, the expression of a specific angiogenesis marker, the $\alpha_v\beta_3$ integrin, is known to correlate with tumor grade.

It has now been found that cationic liposomes bearing a non-peptidic integrin antagonist as a targeting agent can deliver nucleic acids such as genes to angiogenic blood vessels. Appropriately selected nucleic acids can suppress or increase blood vessel growth as desired, and thus provide a means for the treatment of angiogenesis dependent diseases.

SUMMARY OF THE INVENTION

Targeting liposomes that include a non-peptidic integrin receptor antagonist and a nucleic acid are provided by the present invention. These targeting liposomes are useful for selective delivery of nucleic acids, such as genes, anti-sense oligonucleotide sequences, DNA, RNA, and the like, to a predetermined target site, e.g., an angiogenic blood vessel in vivo, when introduced either systemically or locally. Selected nucleic acids can be delivered to angiogenic blood vessels in this manner to mediate vascular endothelial cell uptake of the nucleic acids for expression or for anti-sense delivery. Disruption of new blood vessel growth can be achieved. Also, by appropriate selection of the nucleic acid to be delivered, new blood vessel growth can be induced, if desired.

More particularly, an $\alpha_v\beta_3$ integrin receptor targeting liposome is a nanoparticle having a size of no more than about 100 nanometers and is a unilamellar or multilamellar vesicle comprising a cationic amphiphile such as a cationic lipid, a neutral lipid, a targeting lipid that has a $\alpha_v\beta_3$ integrin targeting domain, and a hydrophobic domain, and a nucleic acid such as a gene, an antisense oligonucleotide sequence, a DNA sequence, a RNA sequence, and the like. The targeting liposome, optionally, can also include a neutral lipid. In the targeting lipid, the targeting domain can be directly attached to the hydrophobic domain. Alternatively, the targeting domain can be covalently bound to a hydrophilic linking domain (surface linker), which in turn, is covalently bound to the hydrophobic domain. The nucleic acid is complexed with the cationic amphiphile present in the liposome. The targeting domain includes a non-peptidic $\alpha_v\beta_3$ integrin antagonist.

In the targeting liposome, the cationic amphiphile, such as a cationic lipid, is present in an amount in the range of about 1 to about 50 mole percent and the targeting domain of the targeting lipid is present in an amount in the range of about 1 to about 20 mole percent, based on total moles of lipid in the liposome. The lipids constituting the targeting liposome can have oligomerizable and/or polymerizable functional groups in their respective hydrophobic portions, and at least a portion of such lipids present in the liposome can be crosslinked to one another trough such groups. The cationic lipid can also have crosslinkable groups, if desired. Alternatively, the cationic lipid can be free from crosslinkable groups.

The present targeting liposomes can be utilized for delivery of nucleic acids to treat cancer, inflammatory diseases, ocular diseases, and the like. Such targeting liposomes can also be utilized to deliver genes to identify therapeutic targets in blood vessels.

The targeting liposomes of this invention are multibinding nanoparticles no larger than about 250 nanometers, preferably about 40 to about 100 nanometers, which include a cationic lipid or cytofectin, together with a nucleic acid complexed therewith. A preferred targeting lipid can be represented as L-X-K, where L is a targeting domain, e.g., an integrin receptor antagonist such as a $\alpha_v\beta_3$ receptor antagonist, and the like, X is a hydrophilic domain that serves as a surface linker to a hydrophobic domain K. Alternatively, the targeting lipid can be represented by L-K wherein the targeting domain L is directly bound to the hydrophobic domain K.

Non-peptidic integrin receptor antagonists, L, suitable for present purposes, at physiological pH values, are zwitterions that have a cationic group and an anionic group that can interact with or bind to an integrin receptor. The cationic and anionic groups are separated from one another by a spacer group, such as a bivalent aromatic group. The spacing between the cationic group and the anionic group on the receptor antagonist molecule is in the range of about 10 to about 100 Angstroms, and can be provided by alkoxybenzoic acids, bicyclic or tricyclic compounds, spirocyclic compounds, and the like, as long as a cationic group and an anionic group spaced therefrom are available to interact with an integrin receptor at physiologic pH values. Suitable integrin receptor antagonists can be represented schematically as follows:

An illustrative non-peptidic $\alpha_v\beta_3$ receptor antagonist is represented by the formula wherein the free amino group (NH$_2$) is available to covalently bind the antagonist to hydrophobic domain of the liposome, either directly, or through a surface linker group.

Other suitable, non-peptidic $\alpha_v\beta_3$ receptor antagonists that are useful for present purposes when bound to a hydrophilic domain of a targeting lipid are described in U.S. Pat. No. 5,561,148, No. 5,776,973 and No. 6,204,280, and in patent publications WO 00/63178, WO 01/10841, WO 01/14337, WO 01/14338, WO 97/45137, WO 98/35949 and WO 00/26212.

The combination of the non-peptidic integrin receptor antagonist L and the optional surface linker X constitute an $\alpha_v\beta_3$ receptor targeting molecule or group suitable for conjugation to a nucleic acid carrier, such as a cationic liposome and the like. The resulting targeting liposome is then associated with a predetermined nucleic acid, e.g., a gene, by complexing therewith.

BRIEF DESCRIPTION OF DRAWINGS

In the drawings,

FIG. 15 depicts photomicrographs demonstrating in vivo delivery to blood vessels in a mouse eye, of a gene encoding GFP, by intravitreal injection of a targeting liposome of the invention bound to the gene;

DESCRIPTION OF PREFERRED EMBODIMENTS

Figure 1:
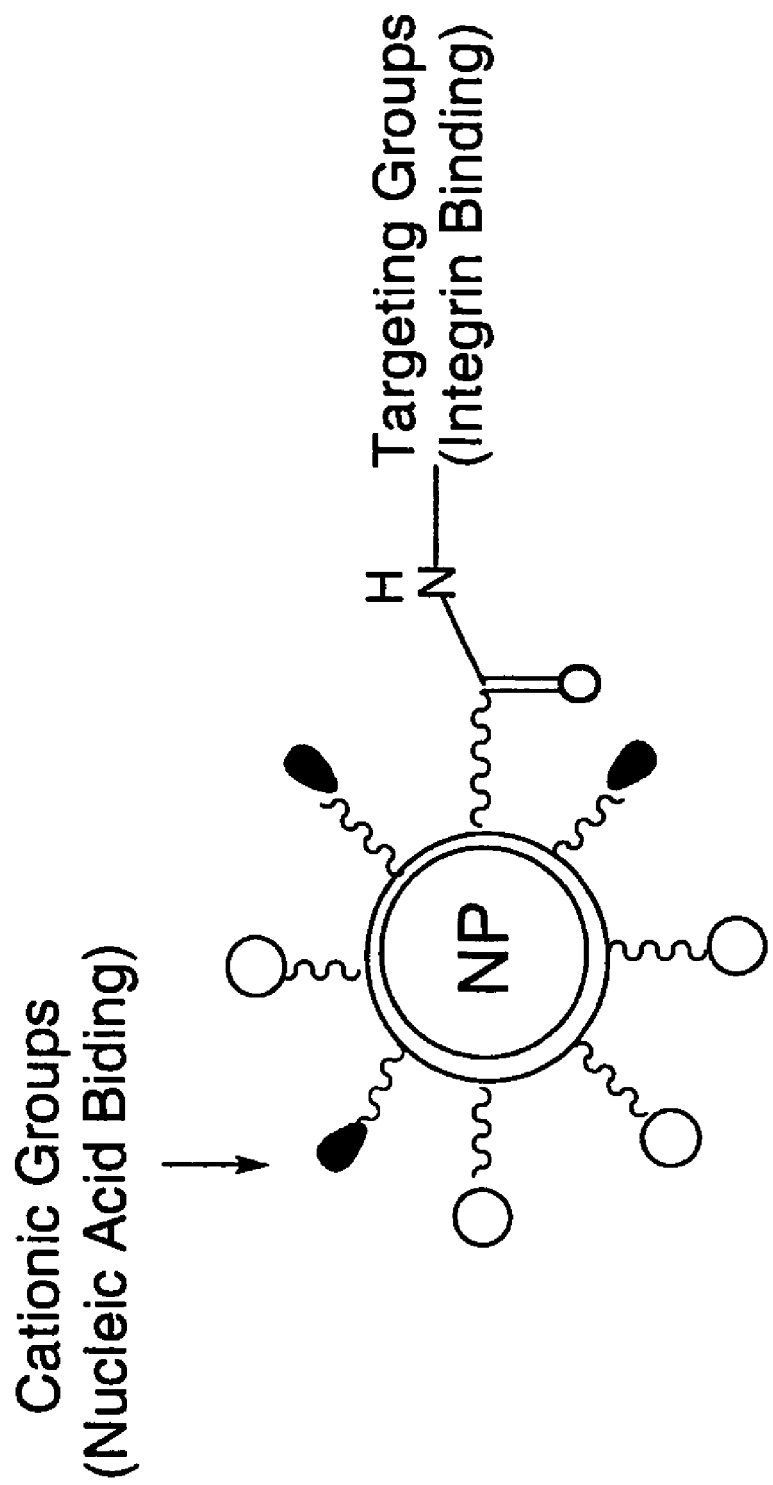
FIG. 1 schematically illustrates a targeting liposome of the present invention.

The targeting liposomes of the present invention are illustrated in FIGS. 1-3 and 18, and are constituted by an integrin receptor antagonist, e.g., an $\alpha_v\beta_3$ receptor antagonist, bound to a lipid, and a carrier for a nucleic acid, e.g., a cationic amphiphile such as a cationic lipid. The liposome can also contain a neutral or zwitterionic filler lipid.

The targeting lipid has a targeting domain which includes an $\alpha_v\beta_3$ integrin receptor antagonist covalently bound to a hydrophobic domain. The targeting domain can be bound directly to the hydrophobic domain, or the targeting domain can be bound to a hydrophilic domain such as a linker group (surface linker), which in turn, is bound to a hydrophobic domain.

Integrin receptor antagonists suitable for the present purposes are zwitterions at physiological pH values and have a cationic group and an anionic group that can interact with or bind to an integrin receptor. The cationic and anionic groups are separated from one another by a spacer group, such as a bivalent aromatic group. The spacing between the cationic group and the anionic group on the receptor antagonist molecule is in the range of about 10 to about 100 Angstroms, and can be provided by p-alkoxybenzoic acids, bicyclic or tricyclic compounds, spirocyclic compounds, and the like, as long as a cationic group and an anionic group spaced therefrom are available for interaction with an integrin receptor at physiologic pH values.

The term "aryl," as used herein and in the appended claims, means a hydrocarbon radical containing at least one 6-carbon aromatic ring, and which can further contain linear, branched, or cyclic hydrocarbon substituents. The term "heteroaryl" means a radical comprising at least one carbon-heteroatom containing aromatic ring, and which can further contain linear, branched, or cyclic hydrocarbon substituents, wherein the heteroatom can be any element selected from the groups designated by the IUPAC as 15 (nitrogen group) and 16 (oxygen group) of the periodic table, including aromatic heterocyclic radicals of such compounds as are disclosed in L. A. Paquette, *Principles of modern Heterocyclic Chemistry*, Benjamin/Cummings Publishing Company, Inc. (1968), the relevant disclosures of which are incorporated herein by reference. When referred to herein, aryl and heteroaryl groups can be unsubstituted or can be substituted.

The term "heterocyclic," as used herein and in the appended claims, means a radical comprising at least one carbon-heteroatom containing non-aromatic ring, and which can further contain linear, branched, or cyclic hydrocarbon substituents, wherein the heteroatom can be any element selected from the groups designated by the IUPAC as 15 (nitrogen group) and 16 (oxygen group) of the periodic table, including non-aromatic heterocyclic radicals of such compounds as are disclosed in Paquette, supra, the relevant disclosures of which are incorporated herein by reference. Heterocyclic groups can be unsubstituted or can be substituted with alkyl groups or with reactive functional groups such as halogens, amino groups, hydroxyl groups, carboxylic acid groups, sulfonic acid groups, and the like.

The term "alkyl," as used herein and in the appended claims, refers to a hydrocarbon moiety, which can be linear, branched, or can contain a carbocyclic ring structure.

The term "alkenyl," as used herein and in the appended claims, refers to an alkyl group having at least one carbon-carbon double bond.

The term "alkynyl," as used herein and in the appended claims, refers to an alkyl group having at least one carbon-carbon triple bond.

The term "substituted," as used herein and in the appended claims, means replacement of one or more hydrogen atoms of one of the above radicals with an alkyl group, a phenyl group, or a functional group such as a hydroxyl, alkoxyl, amino, nitroso, nitro, azo, azido, amido, carboxyl, oxo, thiol, sulfoxyl, sulfonyl, phosphinyl, phosphonyl, fluoro, chloro, bromo, iodo, and like groups, such as are described in R. Panico et al. Ed., *A Guide To IUPAC Nomenclature of Organic Compounds*, Blackwell Science Ltd. (1993), the relevant disclosures of which are incorporated herein by reference.

The term "liposome," as used herein and in the appended claims, refers to a globule whose walls are lipid molecules that may or may not be co-polymerized to one another.

The term "lipid," as used herein and in the appended claims, refers to any member of the groups of oils, fats, fat-like substances that characteristically are soluble in relatively non-polar solvents, but are only sparingly soluble in aqueous solvents. Lipids constitute on of the four major classes of compounds found in living tissues and include fatty acids, neutral fats such as triacylglycerols, fatty acid esters, and soaps, long chain (fatty) alcohols and waxes, sphingoids and other long chain bases, glycolipids, phospholipids, sphingolipids, carotenes, polyprenols, sterols, and the like, as well as terpenes and like isoprenoids.

The term "cytofectin," as used herein and in the appended claims, denotes a cationic lipid suitable for gene delivery and expression, made up of a cationic head group attached by a linker to a hydrophobic domain or moiety.

The term "neutral," as used herein and in the appended claims, with reference to lipids includes uncharged lipids, e.g., cholesterol and the like, as well as zwitterionic lipids, e.g., dioleoylphosphatidyl ethanolamine, dioleoylphosphatidyl choline, and the like.

The term "cholesteryl," as used herein and in the appended claims, refers to steroidal hydrocarbon moieties derived from, or structurally similar to cholesterol.

The term "integrin receptor antagonist," as used herein and in the appended claims, refers to a non-peptidic compound that selectively binds to and antagonizes a receptor of an integrin, e.g., the $\alpha_v\beta_3$ receptor, the $\alpha_v\beta_5$ receptor, the $\alpha_v\beta_6$ receptor, and the like.

A illustrative such $\alpha_v\beta_3$ antagonist compound is represented by the formula

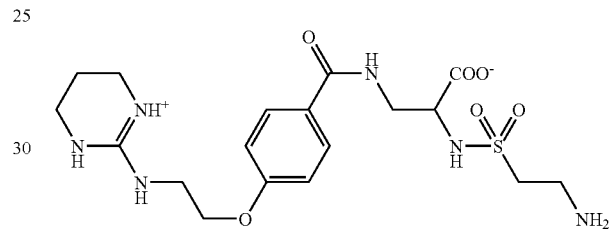

wherein the free amino group ($NH_2$) is available to covalently bind the antagonist to a hydrophobic domain of the liposome through a surface linker group such as a carboxylic and or other suitable active group.

Other illustrative, non-peptidic $\alpha_v\beta_3$ receptor antagonists that are useful for present purposes, when bound directly or indirectly to a hydrophobic domain of a targeting lipid, are described in U.S. Pat. No. 5,561,148, U.S. Pat. No. 5,776,973 and U.S. Pat. No. 6,204,280, and in patent publications WO 00/63178, WO 01/10841, WO 01/14337, WO 01/14338, WO 97/45137, WO 98/35949 and WO 00/26212, the relevant disclosures of which are incorporated herein by reference. Such $\alpha_v\beta_3$ receptor antagonists are illustrated below:

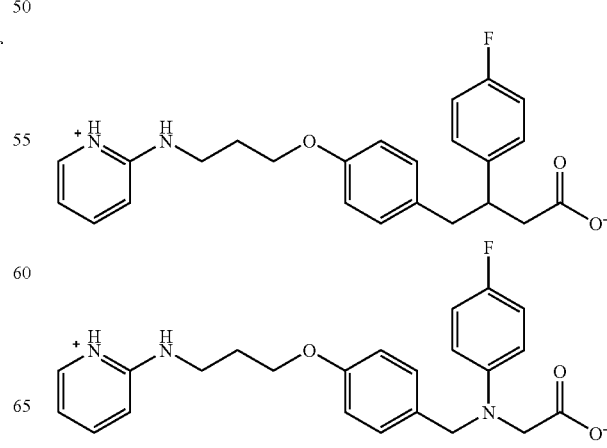

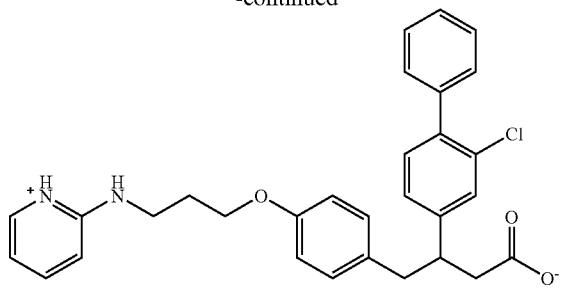

and the like, as described in WO 01/14338;

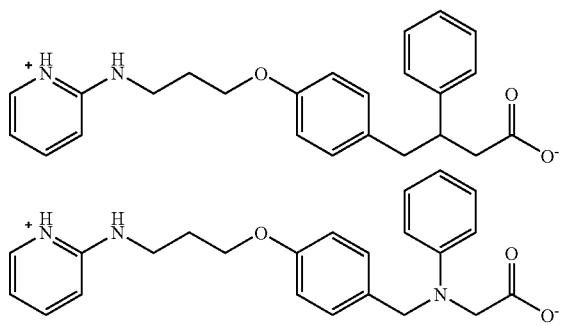

and the like, as described in WO 01/14337;

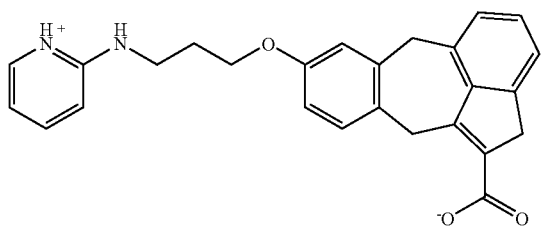

and the like, as described in WO 00/63178;

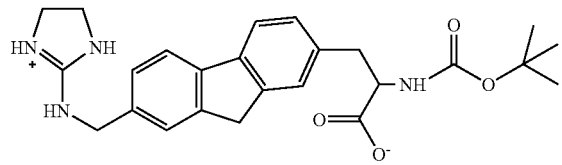

and the like, as described in WO 01/10841; provided such compounds include, or are modified to include, a functional group or a bridging group that can be reacted with a surface linker or hydrophobic domain to form a targeting lipid. Such modifications are well know in the chemical art. For example, one of the aromatic portions of compounds illustrated above can be chemically substituted with an amino, hydroxy, or thiol group to afford a means of attachment to a surface linker. Alternatively, the aromatic groups can be substituted with a carboxylic acid and the surface linker can be an amino-substitute, for example.

The non-peptidic integrin receptor antagonist is covalently attached to the hydrophilic surface linker or directly to the hydrophobic domain using conventional chemical techniques providing for covalent linkage of the antagonist to the surface linker or hydrophobic domain. Reaction chemistries resulting in such linkages are well known in the art and involve the use of complementary functional groups on the surface linker or hydrophobic domain and the integrin antagonist ligand. Preferably, the complementary functional groups on the surface linker or hydrophobic domain are selected relative to the functional groups available on the ligand for bonding, or which can be introduced onto the ligand for bonding. Again, such complementary functional groups are well known in the art. For example, reaction between a carboxylic acid and a primary or secondary amine in the presence of suitable, well-known activating agents, results in formation of an amide bond which can covalently link the ligand to the surface linker or hydrophobic domain; reaction between an amine group and a sulfonyl halide group results in formation of a sulfonamide bond which can covalently link the ligand to the surface linker or hydrophobic domain; and reaction between an alcohol or phenol group and an alkyl or aryl halide results in formation of an ether bond which can covalently bind the integrin antagonist ligand to the surface linker or hydrophobic domain.

Alternatively, the integrin receptor antagonist can include a hydrophobic domain such as a $C_{18}$-$C_{30}$ alkyl group, a $C_{18}$-$C_{30}$ alkenyl group, a $C_{18}$-$C_{30}$ alkynyl group, a cholesteryl group, and the like.

The hydrophobic domain, with or without an intervening surface linker is attached to the integrin receptor antagonist at a position that retains the receptor binding site interaction and specifically which permits the antagonist to orient itself to bind to the integrin receptor binding site. Such positions and synthetic protocols for linkage are well known in the art.

Preferred $\alpha_v\beta_3$ integrin receptor antagonists that include, or can be covalently attached to, a hydrophobic domain are represented by formulas (I) and (II):

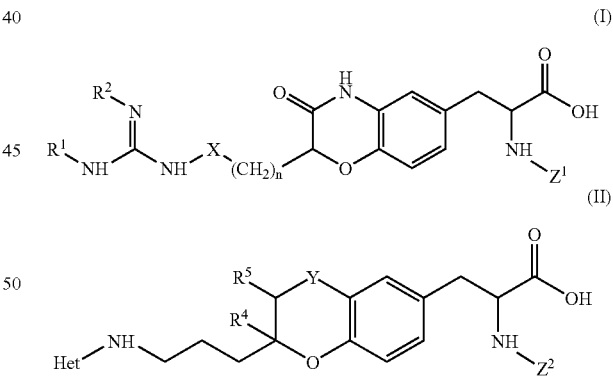

wherein in formula (I), $R^1$ and $R^2$ are each hydrogen, or together form a bridging 1,2-phenylene ($C_6H_4$) group or a bridging ethylene group (—CH=CH—); X is —C(O)— or a covalent bond; n is 1, 2, or 3; $Z^1$ is —C(O)—$R^3$; —C(O)O$R^3$, or SO$_2$R$^3$; and $R^3$ is phenyl, substituted-phenyl, pyridyl, benzyl, substituted-benzyl, $C_1$-$C_4$ haloalkyl, $C_2$-$C_{30}$ alkyl, $C_2$-$C_{30}$ alkenyl, $C_2$-$C_{30}$ alkynyl, or cholesteryl; and wherein in formula (II), $R^4$ and $R^5$ are each hydrogen, or together form a covalent bond; Y is —C(O)— or —CH$_2$—; $Z^2$ is —C(O)—$R^6$; —C(O)O$R^6$, or SO$_2$R$^6$; $R^6$ is phenyl, substituted-phenyl, pyridyl, benzyl, substituted-benzyl; $C_1$-$C_4$ haloalkyl, $C_2$-$C_{30}$ alkyl, $C_2$-$C_{30}$ alkenyl, $C_2$-$C_{30}$ alkynyl, or cholesteryl; and Het is 2-pyridyl or 2-imidazolyl.

Non-limiting examples of integrin receptor antagonists of formula (I) include compounds Ia, Ib, Ic, Id, Ie, and If, below. The preparation of these particular compounds is described in PCT publication WO 98/35949.

Non-limiting examples of integrin receptor antagonists of formula (II) include compounds Ia, IIb, IIc, IId, IIe, and IIf, below. The preparation of these particular compounds is described in PCT publication WO 00/26212.

(Ia)

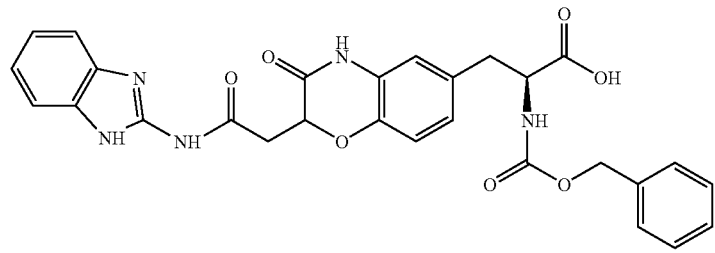

MW = 543.53

(Ib)

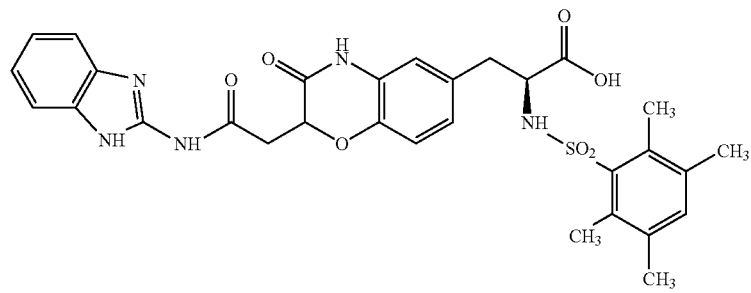

MW = 605.67

(Ic)

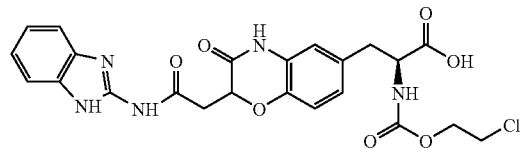

MW = 515.91

(Id)

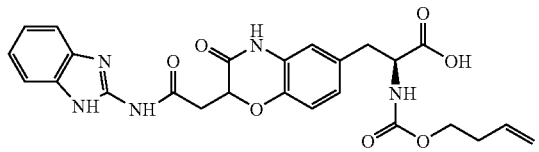

MW = 507.50

(Ie)

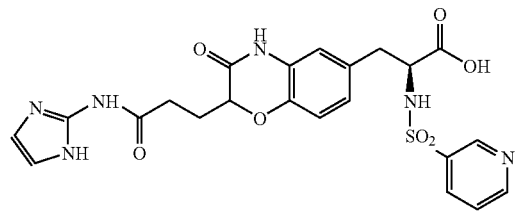

MW = 514.52

(If)

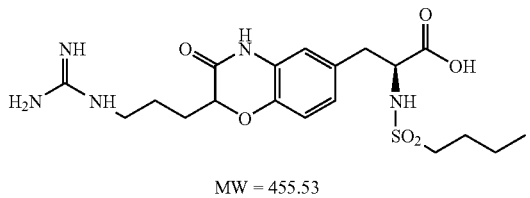

MW = 455.53

(IIa)

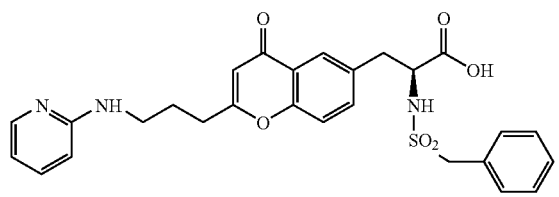

MW = 521.60

(IIb)

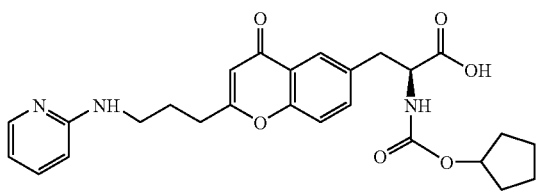

MW = 479.53

-continued

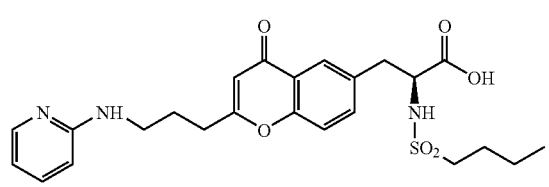

MW = 487.57 (IIc)

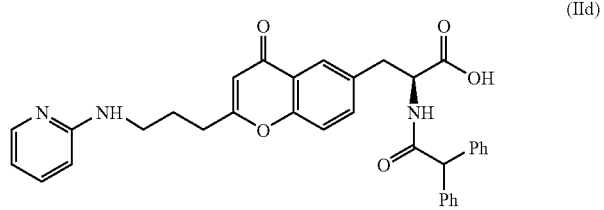

MW = 561.63 (IId)

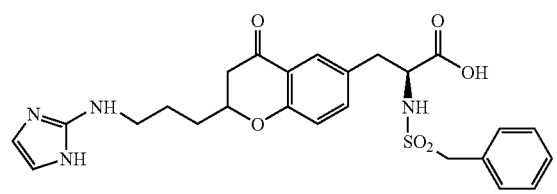

MW = 512.59 (IIe)

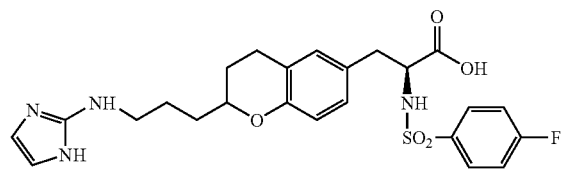

MW = 502.56 (IIf)

Preferred $\alpha_v\beta_3$ integrin receptor antagonists have a molecular mass (MW) in the range of about 200 to about 800 Daltons, more preferably 450 to about 610 Daltons, when not covalently attached to a hydrophobic domain of a targeting lipid.

The $\alpha_v\beta_3$ integrin receptor antagonist, when covalently attached to, or including a hydrophobic domain, in combination with a cationic lipid, provides a cationic liposome that is biocompatible and substantially non-immunogenic. The biological activity of the targeting liposome may be sensitive to the valency, geometry, composition, size, flexibility or rigidity, etc. of the hydrophilic surface linker, if present, and in turn, on the overall configuration of the targeting liposome, as well as the, the relative hydrophilicity of the surface linker, and the like. Accordingly, the hydrophilic surface linker, when present, is preferably chosen to maximize the biological activity of the targeting liposome. The surface linker may be chosen to enhance the biological activity of the targeting molecule. In general, the surface linker may be chosen from any organic molecule construct that orients the antagonist to its binding site. In this regard, the surface linker can be considered as a "framework" on which one or more integrin antagonists are arranged in order to bring about the desired orienting result. Orientation can include, for example, presenting the antagonist at a suitable distance from the surface of the liposome to allow effective interaction of the antagonist with the active site of the integrin receptor.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In another preferred embodiment, the ring is a six or ten member ring. In still further preferred embodiments, the ring is an aromatic ring such as, for example, phenyl or naphthyl.

The crystal structure of the extracellular portion of the $\alpha_v\beta_3$ integrin, when associated with an integrin antagonist, is described in Xiong et al., *Science* 296: 151-155 (2002). The $\alpha_v\beta_3$ integrin receptor antagonists utilized in practicing the present invention have a structure that interacts with the $\alpha_v\beta_3$ integrin receptor in a similar manner to the interaction described by Xiong et al.

Different hydrophilic characteristics of the surface linker, as well as the presence or absence of charged moieties on the liposome, can readily be controlled by the skilled artisan. For example, the hydrophobic nature of a surface linker derived from hexamethylene diamine ($H_2N(CH_2)_6NH_2$) or related polyamines can be modified to be substantially more hydrophilic by replacing the alkylene group with a poly(oxyalkylene) group such as poly(ethylene glycol), poly(propylene glycol) and the like.

Properties of the surface linker can be modified by the addition or insertion of ancillary groups into or onto the surface linker, for example, to change the solubility of the liposomes (in water, fats, lipids, biological fluids, etc.), hydrophobicity, hydrophilicity, surface linker flexibility, antigenicity, stability, and the like. For example, the introduction of one or more poly(ethylene glycol) (PEG) groups onto or into the surface linker enhances the hydrophilicity and water solubility of the nanoparticulate liposome, increases both molecular weight and molecular size and, depending on the nature of the surface linker, may increase the in vivo retention time as well. Further, PEG may decrease antigenicity and potentially enhances the overall rigidity of the surface linker.

Ancillary groups that can enhance the water solubility/hydrophilicity of the liposome are useful in practicing this invention. Thus, it is within the scope of the present invention to use ancillary groups such as, for example, small repeating units of ethylene glycols, propylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like, to enhance the water solubility and/or hydrophilicity of the liposome of this invention. In preferred embodiments, the ancillary group used to improve water solubility/hydrophilicity is a polyether. The ancillary group can be attached to a surface linker on the targeting lipid, or can be attached to other lipids in the liposome such as the cationic lipid or a neutral filler lipid, for example.

The incorporation of lipophilic ancillary groups within the structure of the surface linker to enhance the lipophilicity and/or hydrophobicity of the liposomes described herein is also within the scope of this invention. Lipophilic groups useful with the surface linkers of this invention include, by way of example only, unsubstituted or substituted aryl and heteroaryl groups, but are at least substituted with a group which allows their covalent attachment to the surface linker. Other lipophilic groups useful with the surface linkers of this invention include fatty acid derivatives that do not form bilayers in aqueous medium until relatively higher concentrations are reached.

The flexibility of the surface linker can be manipulated by the inclusion of ancillary groups that are bulky and/or rigid. The presence of bulky or rigid groups can hinder free rotation about bonds in the surface linker, bonds between the surface linker and the ancillary group(s), or bonds between the surface linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the presenter surface linker into a configuration affording the maximum distance between each of the like charges. The energetic cost of bringing the like-charged groups closer to each other will tend to hold the surface linker in a configuration that maintains the separation between the like-charged ancillary groups. Additionally, ancillary groups bearing opposite charges will tend to be attracted to their oppositely charged counterparts and potentially may enter into both inter- and intra molecular ionic bonds. This non-covalent mechanism will tend to hold the surface linker into a conformation which allows bonding between the oppositely charged groups. The addition of ancillary groups which are charged, or alternatively, bear a latent charge when deprotected, following addition to the surface linker, include deprotection of a carboxyl, hydroxyl, thiol or amino group by a change in pH, oxidation, reduction or other mechanisms known to those skilled in the art which results in removal of the protecting group, is within the scope of this invention.

Rigidity may also be imparted by internal hydrogen bonding or by hydrophobic collapse.

Bulky groups can include, for example, large atoms, ions (e.g., iodine, sulfur, metal ions etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to provide greater rigidity to the structure than are straight-chain species of similar molecular weight.

In some embodiments, rigidity is imparted by the presence of cyclic groups (e.g., aryl, heteroaryl, cycloalkyl, heterocyclic, etc.). In other embodiments, the surface linker comprises one or more six-membered rings. In still other embodiments, the ring is an aryl group such as, for example, phenyl or naphthyl.

The appropriate selection of a surface linker group providing suitable orientation, restricted/unrestricted rotation, the desired degree of hydrophobicity/hydrophilicity, etc. is well within the skill of the art. Eliminating or reducing antigenicity of the nanoparticles described herein is also within the skill of the art. In certain cases, the antigenicity of a nanoparticle may be eliminated or reduced by use of groups such as, for example, poly(ethylene glycol) groups.

The nucleic acid carrier is a cationic amphiphile such as a cationic lipid, a cationic liposome, or a micelle having cationic groups, which is capable of binding to a nucleic acid usually by interaction with negatively charged nucleic acid sequences to form complexes capable of entering the cell. Targeting liposomes are illustrated in FIGS. 1, 2, 3, 17 and 18.

Cationic lipids suitable for present purposes (cytofectins) are illustrated by 1,2-dioleoyloxy-3-(N,N,N-trimethylammonium)propane chloride (DOTAP), dimethyldioctadecylammonium bromide (DDAB), dioleoyldimethylammonium chloride, dioleoyl-L-α-phosphatidylethanolamine (DOPE), N-cholesteryloxycarbaryl-3,7,12-triazapentadecane-1,15-diamine (CTAP), and the like. A preferred cationic lipid is DOTAP. Other suitable cationic lipids are described in Miller, *Angew. Chem. Int. Ed.* 37:1768-1785 (1998), hereinafter "Miller", and Cooper et al., *Chem. Eur. J.* 4(1): 137-151 (1998), incorporated herein by reference to the extent pertinent.

The targeting liposome of the present invention can be crosslinked, partially crosslinked, or free from crosslinking. Crosslinked liposomes can include crosslinked as well as non-crosslinked components.

An exemplary non-crosslinked targeting liposome of the present invention is a lipid mixture including DOTAP (cationic lipid), cholesterol (neutral lipid), polyethylene glycol (a hydrophilic ancillary component) such as PEG-350 (a polyoxyethylene having 350 oxyethylene repeating units) and a nonpeptidic integrin receptor antagonist covalently bound to or including a lipid. Preferably, the ratio of DOTAP to cholesterol to polyethylene glycol is about 1:1:0.12 respectively, and the nonpeptidic integrin receptor antagonist-containing lipid (integrin targeting lipid) is included in an amount sufficient to provide a relatively high avidity for $\alpha_v\beta_3$ integrin. Preferably the targeting liposome includes the integrin targeting lipid in an amount in the range of about 1 to about 20 mol % based on total moles of lipid components in the liposome, more preferably about 8 to about 12 mole %.

A preferred crosslinked targeting liposome of the present invention includes a polymerizable zwitterionic or neutral lipid, a polymerizable integrin targeting lipid and a polymerizable cationic lipid suitable for binding a nucleic acid.

In another preferred embodiment, the crosslinked targeting liposome includes a polymerizable zwitterionic or neutral lipid, a polymerizable integrin targeting lipid and a non-polymerizable cationic lipid.

The liposome containing polymerizable lipids can be crosslinked, for example, by addition of a suitable free radical polymerization initiator, by irradiation with a suitable wavelength of ultraviolet light, or by other methods known in the polymerization art.

Suitable cationic liposomes or cytofectins are commercially available and can also be prepared as described in Sipkins et al., *Nature Medicine*, 1998, 4(5):(1998), 623-626 or as described in Miller, supra.

Cationic liposomes can be formed either from a single cationic amphiphile or from a combination of a cationic amphiphile and a neutral lipid, for example, from 3,3-[N—(N',N'-dimethylaminoethane)carbamoyl]cholesterol and dioleyl L-α-phosphatidyl-ethanolamine.

Hydrophilic characteristics derive from the presence of a phosphate, a phosphonate, a carboxylate, a sulfate, a sulfonate, a sulfhydryl, an amino, a nitro, a hydroxyl, or other like groups, which are well known in the art. Hydrophobicity can be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids. Representative examples of phosphoglycerides include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Compounds that lack phosphorous-containing groups, such as the sphingolipid and glycosphingolipid families, are also within the group designated as lipid. Additionally, the amphipathic lipids described above may be mixed with other lipids including triglycerides and sterols such as cholesterol, modified cholesterols, and the like.

The integrin receptor antagonists can include a hydrophobic domain or be attached to the surface linker or directly to a hydrophobic domain at any suitable position, for example, at the termini of a linear chain or at any intermediate position thereof, as long as the attachment does not interfere with binding of the antagonist to the integrin receptor. The integrin receptor antagonists can also include, or be provided with, an optional divalent bridging group to facilitate attachment to the surface linker, if desired.

FIG. 1 schematically illustrates a targeting liposome as a spherically shaped particle having nucleic acid binding sites and integrin targeting sites on the surface of the particle.

Figure 2:
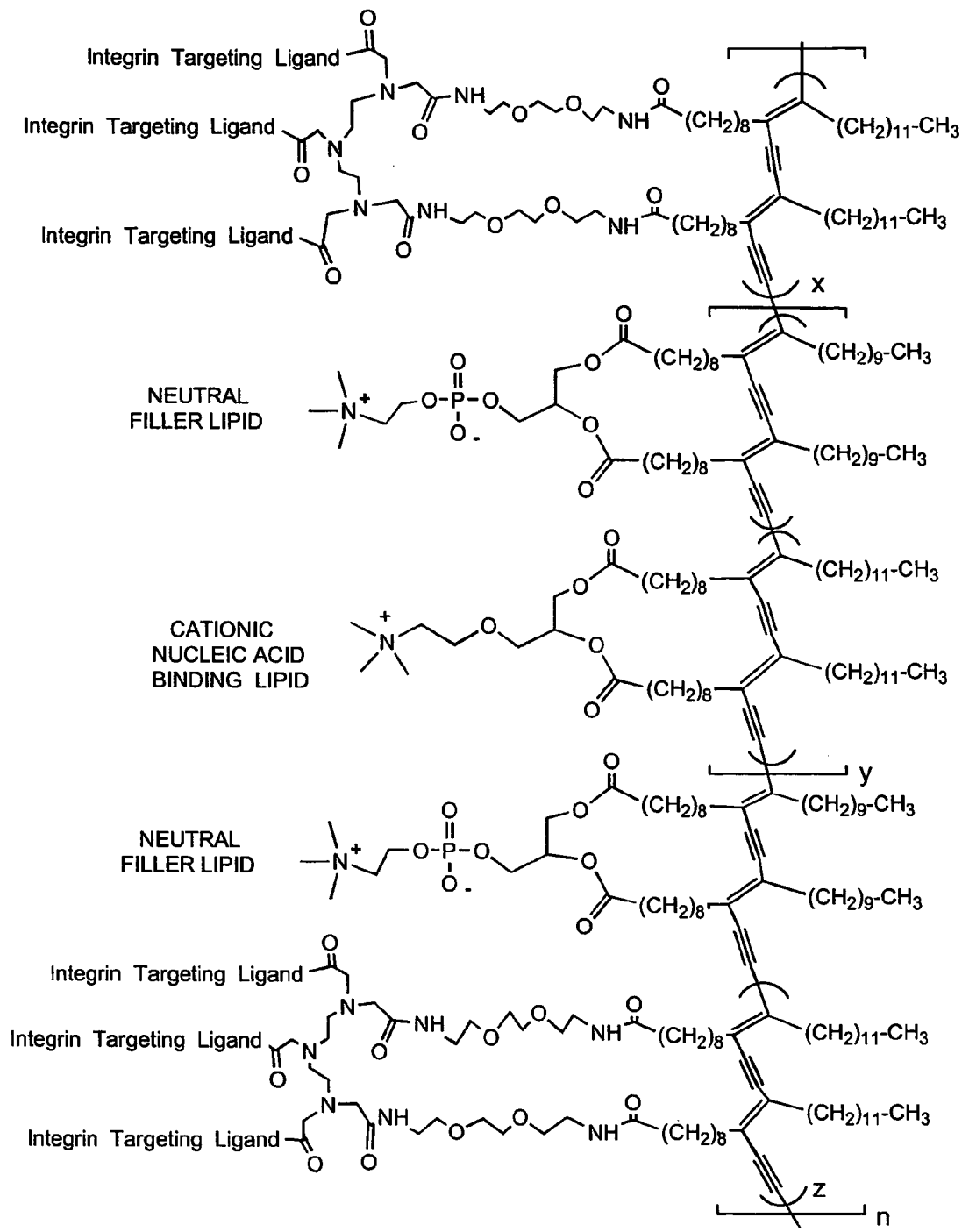
FIG. 2 is an illustration of a crosslinked targeting liposome of the present invention.
Figure 3:
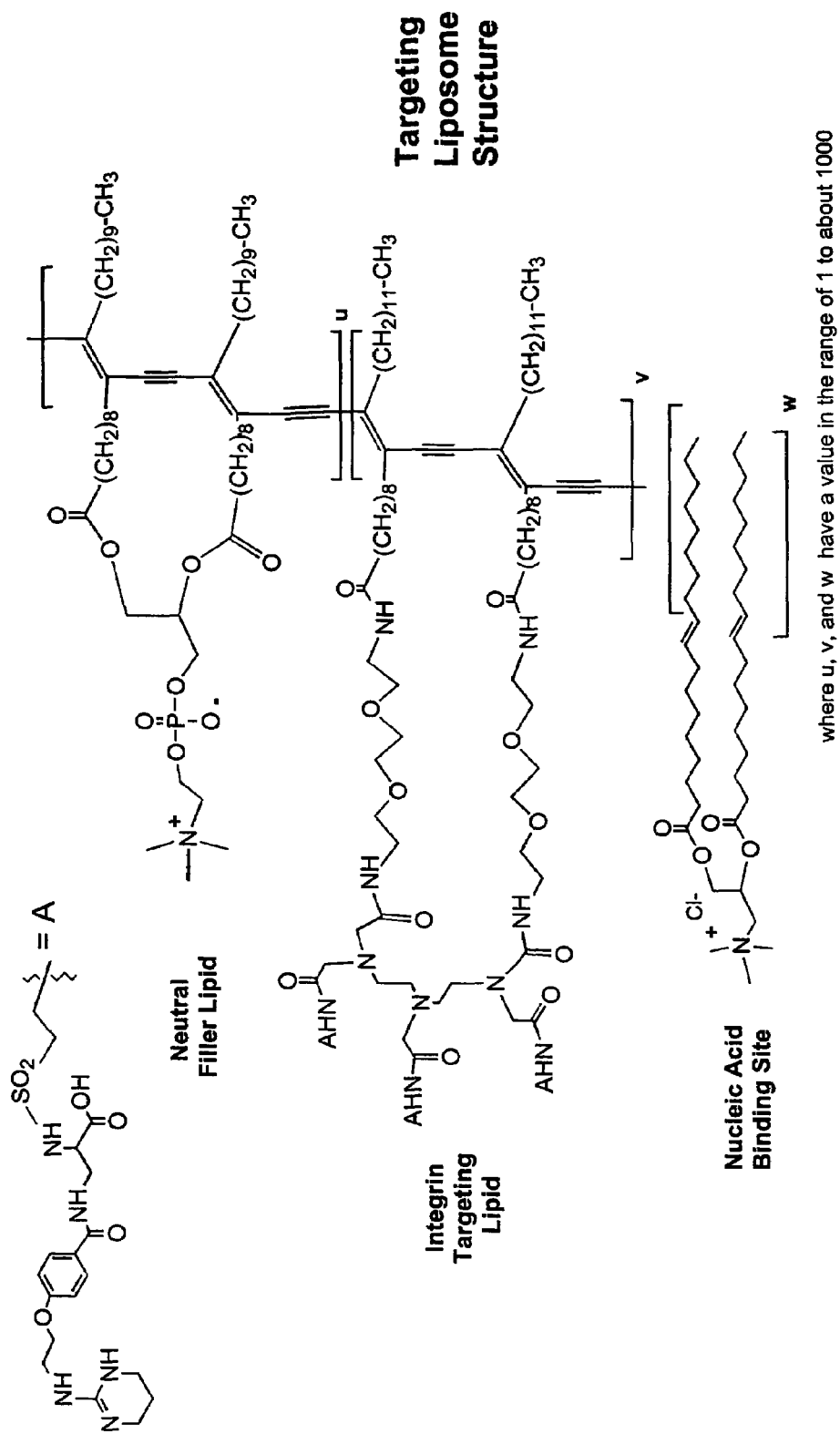
FIG. 3 is an illustration of another crosslinked targeting liposome of the present invention.
Figure 4:
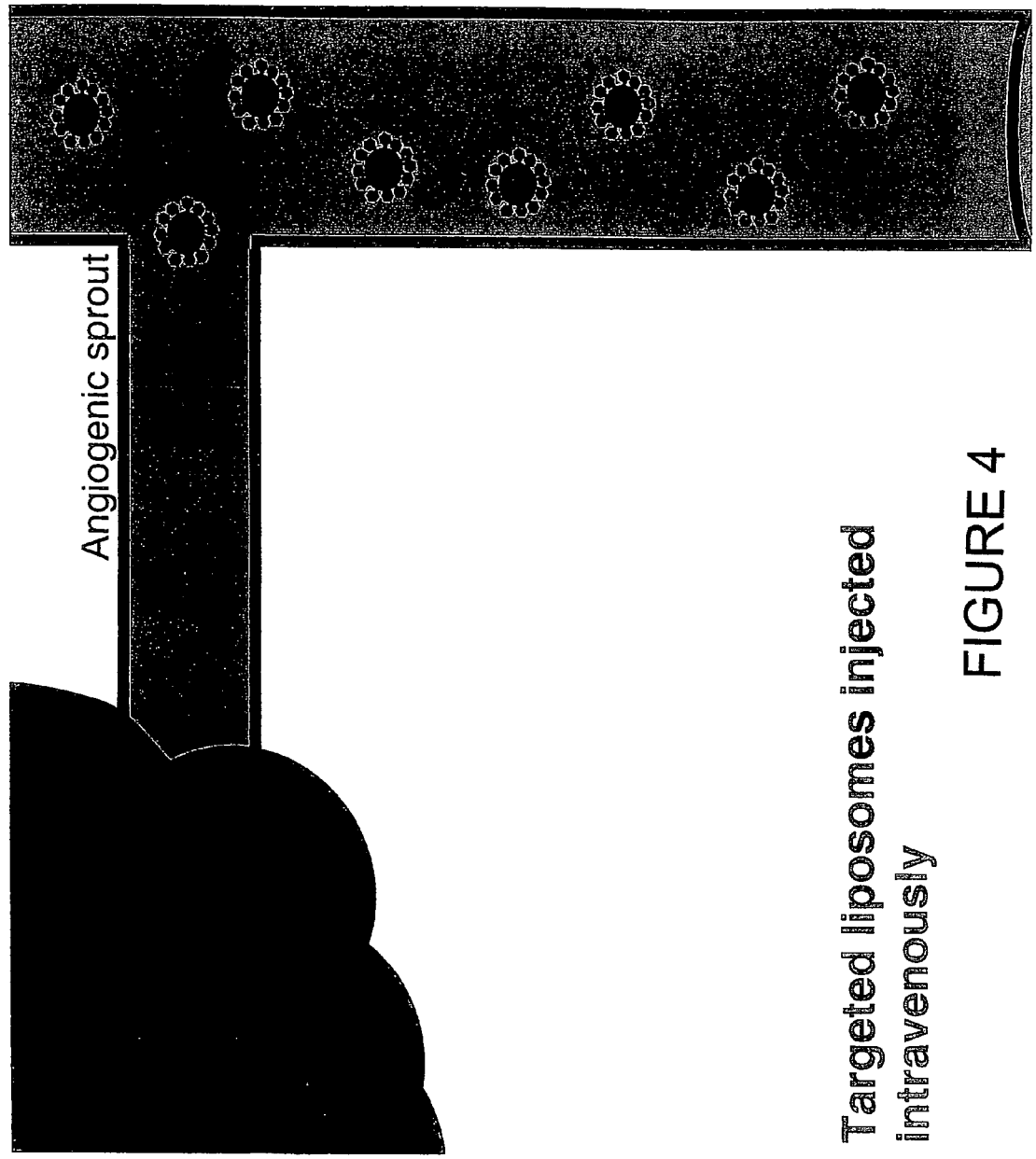
FIG. 4 schematically illustrates targeting liposomes circulating systemically.
Figure 5:
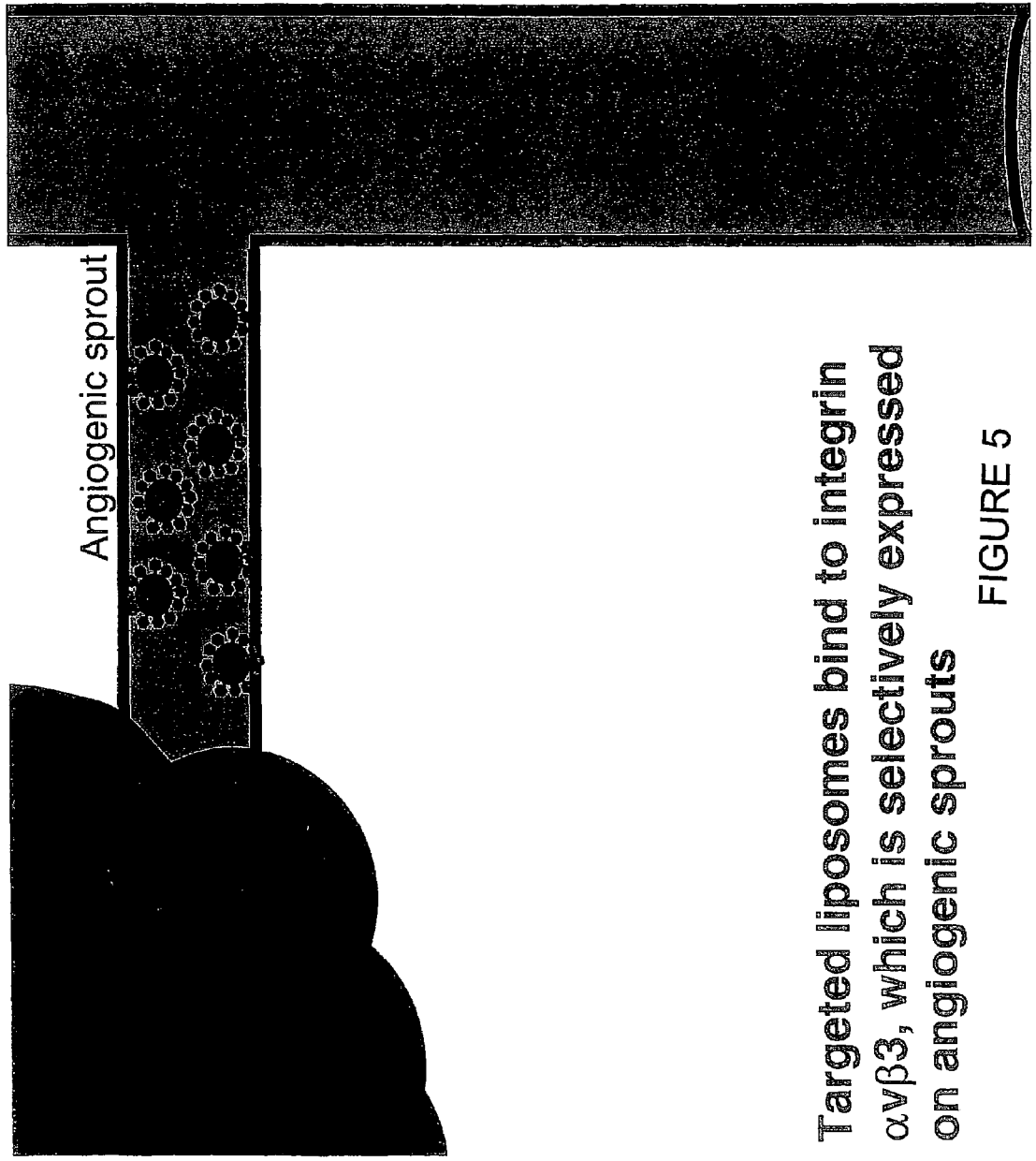
FIG. 5 schematically illustrates targeting liposomes collecting at angiogenic sites.
Figure 6:
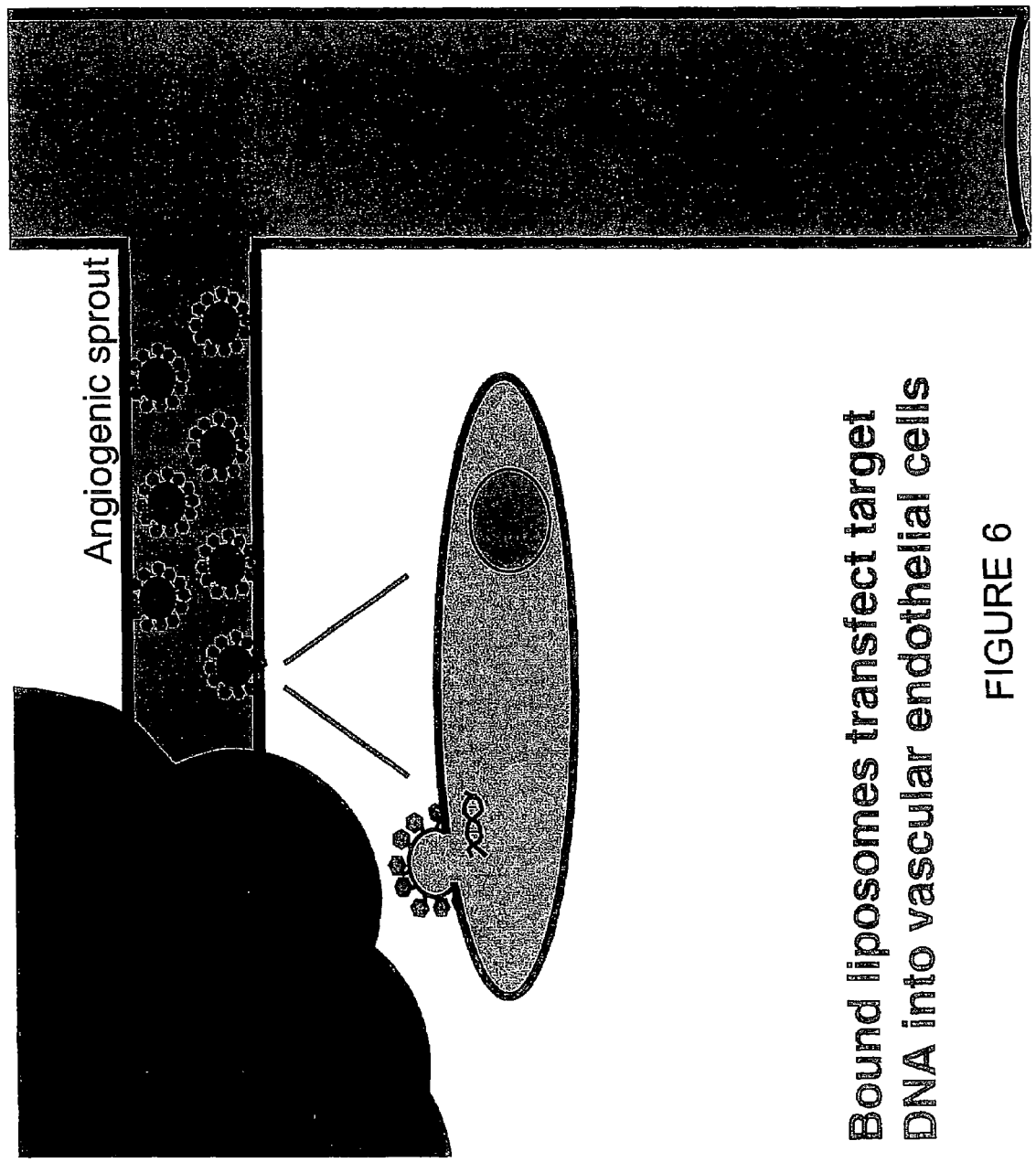
FIGS. 6 and 7 schematically illustrate the delivery of DNA, such as a gene, to targeted cells.
Figure 7:
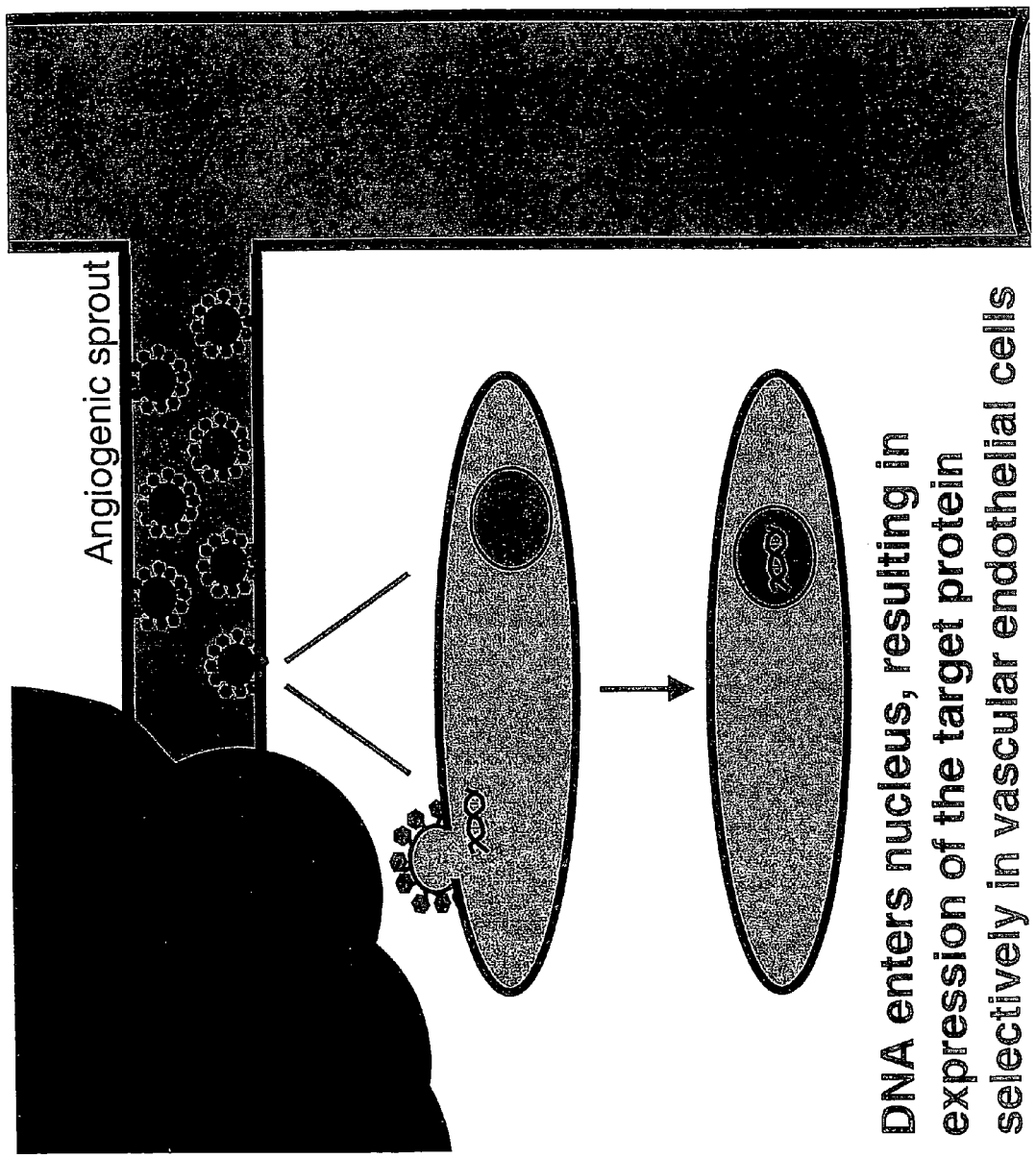

FIG. 2 illustrates a crosslinked targeting liposome of the present invention. FIG. 3 illustrates another crosslinked targeting liposome, wherein the cationic lipid in present in the liposome, but not crosslinked thereto. The preparation of this targeting liposome embodiment is described in detail in the Materials and Methods section hereinbelow. Such a crosslinked liposome presents, on its outer surface, cationic groups derived from the choline moieties, capable of binding nucleic acids, and integrin receptor binding sites derived from the integrin antagonist groups bound to a hydrophilic surface linker.

Nucleic acids can be bound to the crosslinked liposome nanoparticle by contacting a negatively charged nucleic acid with the cationic group present on the liposome, such as by mixing the nucleic acid and the targeting liposome in a pharmaceutically acceptable aqueous medium at physiologic pH. The so-formed nucleic acid complexed targeting liposomes are readily taken up by integrin presenting cells that are contacted with the targeting liposomes both in vitro and in vivo.

The ratio of targeting liposome positive charges-to-nucleic acid negative charges preferably is greater than 1, more preferably at least about 1.2.

For the selective targeting or antagonism of the integrins, such as the $\alpha_v\beta_3$ integrins, the compounds and compositions of the present invention may be administered in a therapeutically effective amount parenterally, orally, by inhalation, or topically in unit dosage form together with pharmaceutically acceptable carriers, vehicles, and adjuvants. The term "parenteral," as used herein, includes intravenous, subcutaneous, intramuscular, intrasternal, intraocular (e.g. intravitreal), and intraperitoneal administration, as well as administration by infusion techniques.

Any suitable route of administration can be utilized. The pharmaceutical composition including a nanoparticle-bound nucleic acid of the present invention is administered in a dose effective for the intended treatment. Therapeutically effective amounts required to treat a particular medical condition, or inhibit the progress thereof, are readily determined by those skilled in the art using preclinical and clinical studies known in the medical arts.

The term "therapeutically effective amount," as used herein, refers to that amount of active ingredient that elicits the biological or medical response of a tissue, system, animal or human, sought by a clinician or a researcher.

The term "inhibit," as used herein, refers to a slowing, interruption, or stoppage of the medical condition, but does not necessarily indicate a total elimination of the condition. A prolonged survivability of a patient, in and of itself, indicates that the medical condition is beneficially controlled.

The dosage regimens for the present targeting liposome-bound nucleic acids or compositions containing the same, are based on several factors such as the age, weight, sex, and type of medical condition of the patient, the severity of the condition, the route of administration, and the antagonist activity of the particular targeting molecule or ligand employed. The dosage regimen may very depending upon the aforementioned factors. Dosage levels on the order of about 0.01 milligram to about 1000 milligrams per kilogram of body weight are useful in treating the aforementioned medical conditions. Preferred dosage levels are in the range of about 0.01 milligram to about 100 milligrams per kilogram of body weight.

For administration by injection, a targeting liposome containing composition embodying the present invention is formulated with a pharmaceutically acceptable carrier such as water, saline, or an aqueous dextrose solution. For injection, a typical daily dose is about 0.01 milligram to about 100 milligrams per kilogram of body weight, injected daily as a single dose or as multiple doses depending upon the aforementioned factors.

To inhibit angiogenesis, for example, a patient in need of angiogenesis inhibition is administered a therapeutically effective amount of a targeting liposome embodying the present invention and carrying a nucleic acid such as a ribonucleic acid (RNA) or a deoxyribonucleic acid (DNA) capable of expressing an angiogenesis inhibiting protein or peptide. The administered nucleic acid then enters a cell nucleus and expresses a target protein in vascular endothelial cells.

The following non-limiting examples are provided to further illustrate the various aspects of the invention. One of skill in the art will recognize that modifications of the examples and illustrated embodiments disclosed herein can be made without departure from the spirit and scope of the invention.

Materials and Methods

Preparation of Nanoparticles.

Figure 17:
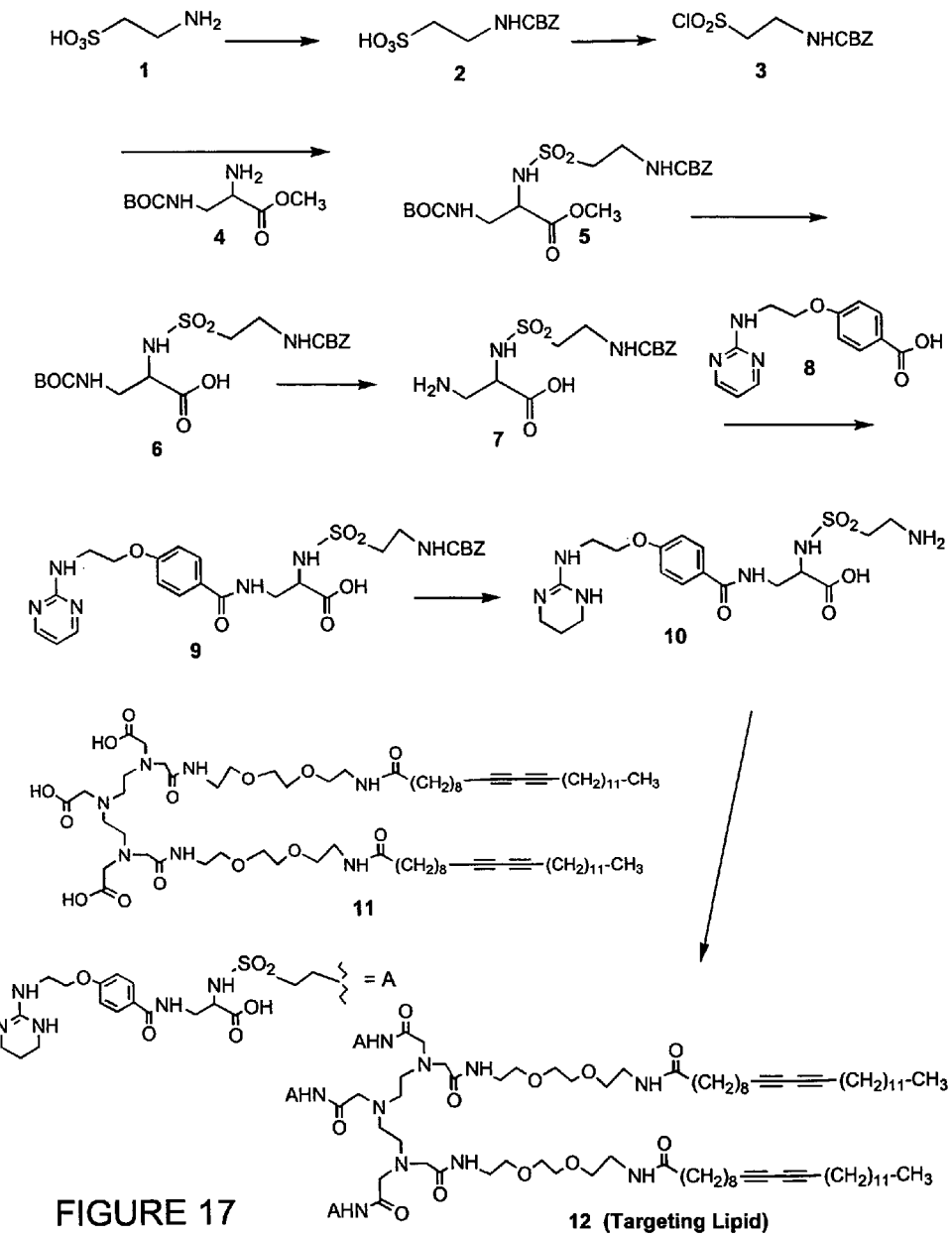
FIG. 17 depicts targeting liposome synthetic Scheme 1, detailing the synthesis of key intermediate trivalent lipid-integrin antagonist conjugate 12.

The construction of multivalent targeting liposomes that bind to the integrins begins with the design and synthesis of the polymerizable lipid integrin targeting molecule 12 (FIG. 17; Scheme 1). The amino group of taurine 1 was protected as its benzyloxycarbonyl (CBZ) derivative to afford 2, followed by formation of the sulfonyl chloride 3 and coupling to the methyl ester of tert-butoxycarbonyl diaminopropionic acid 4 to yield compound 5. Saponification of 5 provided compound 6 and removal of the tert-butoxycarbonyl (BOC) group afforded the key intermediate 7. Coupling of 7 to benzoic acid derivative 8 provided compound 9, which was hydrogenated to deprotect the amine and simultaneously reduce the pyrimidine ring to afford the integrin receptor antagonist-linker conjugate 10. The synthesis of compound 8 has been described previously by Duggan et al. *J. Med. Chem.*, 2000, 43, 3736-3745, the relevant disclosures of which are incorporated herein by reference. Coupling of three equivalents of 10 to the tricarboxylic acid chelator lipid 11 using benzotriazol-1-yloxytris(dimethylamino)phosphonium hexafluorophosphate (BOP) provided the key trivalent integrin antagonist lipid 12. The preparation of Compound 11 has been previously described by Storrs et al. *J. Magn. Reson. Imaging*, 1995, 5, 719-724, the relevant disclosure of which is incorporated herein by reference. Treatment of 11 with sodium methoxide in methanol afforded compound 15 (i.e. the trisodium salt of 11). The europium-chelator lipid complex 14 was synthesized by heating 15 with a solution of europium trichloride as described by Storrs, et. al., supra.

Figure 18:
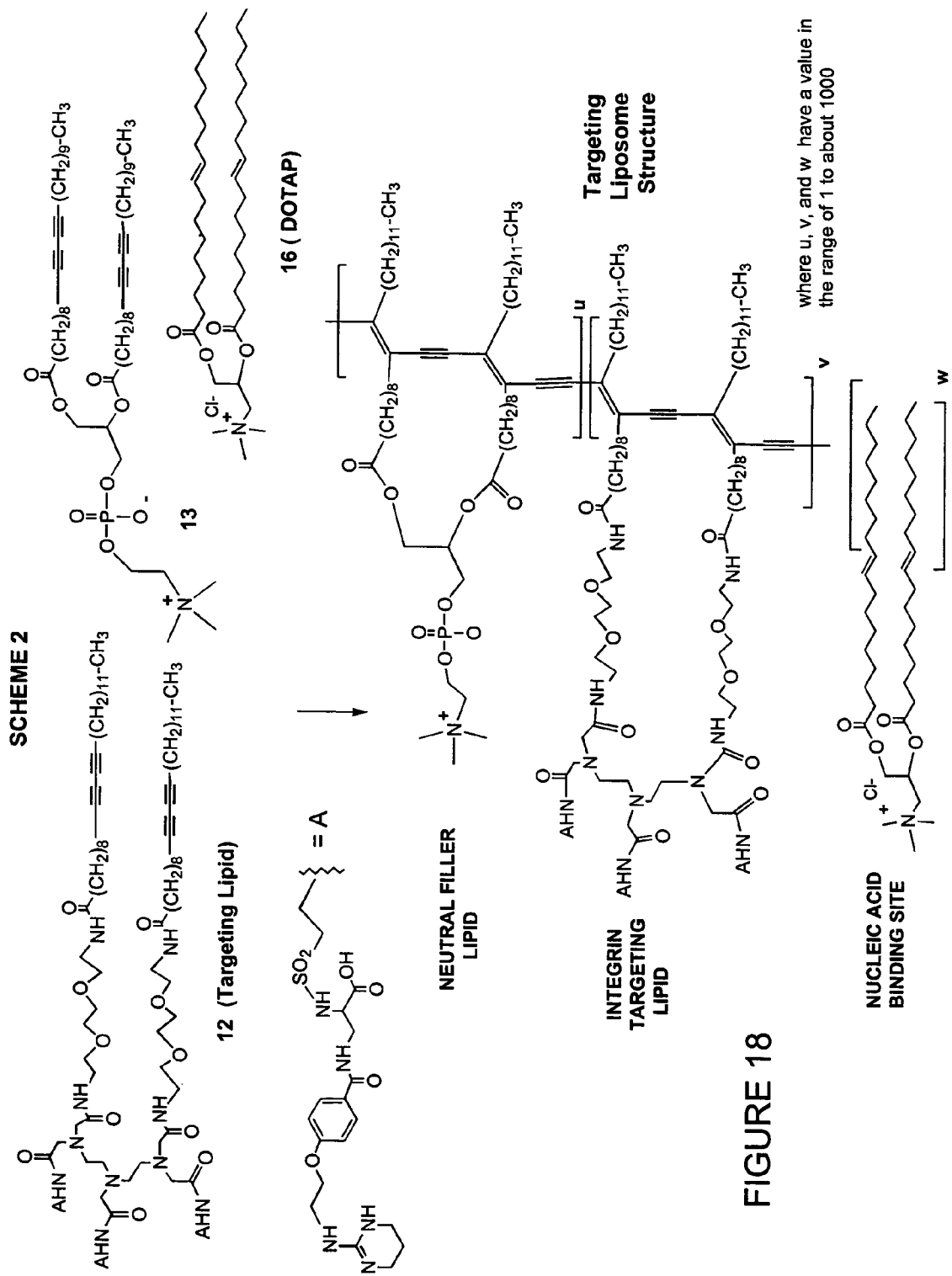
FIG. 18 depicts targeting liposome synthetic Scheme 2, which outlines the formation of nanoparticulate targeting liposomes (NPs) by self-assembly and polymerization of the appropriate lipids from trivalent lipid-integrin antagonist conjugate 12.

Scheme 2, in FIG. 18, outlines the formation of crosslinked targeting liposomes (NPs) by self-assembly and polymerization of the appropriate lipids as previously described by Storrs, et. al., supra. Exemplary crosslinked targeting liposomes were synthesized by combining the trivalent lipid-integrin antagonist 12, with diacetylene zwitterionic phospholipid 13, and the europium-chelator lipid complex 14 in a chloroform solution. Compound 14 was added at 1 weight percent to all formulations in order to visualize the particles using fluorescence spectroscopy. To this chloroform solution of lipids was added either the anionic chelator lipid 15 or the cationic lipid 16 (DOTAP) in order to vary the surface charge. The surface density of the integrin antagonist on the NPs was controlled by varying the amount of compound 12 in the liposome.

To form vesicles, the combined lipid solutions were evaporated to dryness and dried under high vacuum to remove any residual solvent to form a lipid film. The dried lipid film was hydrated to a known lipid density (30 mM) using deionized water. The resulting suspension was then sonicated at temperatures above the gel-liquid crystal phase transition ($T_m$ 64° C.), following the procedure of Leaver et al. *Biochim. Biophys. Acta*, 1983, 732, 210-218, using a probe-tip sonicator while maintaining the pH between 7.0 and 7.5. After approximately one hour of sonication the solution became clear. The vesicles were then polymerized by cooling the solution to 0° C. on a bed of wet ice and irradiating the solution at about 254 nm with a hand-held UV lamp for about 2 hours. The resulting liposomes (NP1 through NP6) were yellow-orange in color and had two visible absorption bands centered at 490 nm and 535 nm and arising from the conjugated ene-yne diacetylene polymer. The mean diameter of the NPs were between 40 nm and 50 nm as determined by dynamic light scattering (DLS). The zeta potential was between −42 and −53 mV for NP1 through NP4 (i.e. NP1-NP4 were negatively charged) and +35 and +43 mV for NP5 and NP6 (i.e. NP5 and NP6 were positively charged) respectively (Brookhaven Instruments, Holtsville, N.Y.). The liposomes were stable for months without significant changes in the physical and biological properties when formulated for in vivo applications using 150 mM sodium chloride, 50 mM histidine, and 5% dextrose solutions.

The compositions of liposomes NP1 through NP6 are provided in Table 1 below, expressed as mol % of components 12 (targeting lipid), 13 (zwitterionic lipid), 15 (anionic chelator lipid), and 16 (cationic lipid; DOTAP).

TABLE 1

| | Liposome Compositions NP1–NP6 | | | |
|---|---|---|---|---|
| Liposome | mol % Targeting Lipid | mol % Zwitterionic Lipid | mol % Anionic Lipid | mol % Cationic Lipid |
| NP1 | 10 | 80 | 10 | 0 |
| NP2 | 1 | 89 | 10 | 0 |
| NP3 | 0.1 | 90 | 10 | 0 |
| NP4 | 0 | 90 | 10 | 0 |
| NP5 | 10 | 80 | 0 | 10 |
| NP6 | 0 | 90 | 0 | 10 |

The liposomes were constructed by polymerizing vesicles using 0.1, 1 and 10 mol % of integrin antagonist lipid complex compound 12 and compound 13 as outlined in FIG. 18, with additional materials 14, 15 and 16 incorporated into the liposomes prior to polymerization to vary the surface charge density and allow the liposomes to be visualized by fluorescence. For simplicity, compound 13, which is optional, and comprises only 1 mole % of the liposome, is not shown in FIG. 18. The materials that contained 10 mol % of compound 12 (NP1 and NP5) had the highest affinity for the integrin $\alpha_v\beta_3$ bonding site. In a competitive integrin binding assay using time resolved fluorescence spectroscopy, it took over 100-fold of the free ligand 10 (65 µM) to reduce the binding of NP1s and $\alpha_v\beta_3$ integrin by 50%, despite the fact that NP1 has only the equivalent of 0.5 µM of the integrin antagonist 10 on its surface. In an in vitro assay for inhibition of cell adhesion using $\alpha_v\beta_3$ positive M21 Melanoma cells binding to vitronectin coated plates, the IC50 for the free ligand 10 was 64 µM. In sharp contrast, the IC50 for the anionic particle NP1 was 0.27 µM equivalents of compound 10 on the surface. This represents over 200 times greater avidity to the cell surface when 10 is on the NPs compared to the free ligand. For the cationic particle NP5, the IC50 was 0.35 µM equivalents of compound 10 which is approximately 180 times greater avidity when compared with free ligand as shown in Table 2 below. Thus, regardless of the surface charge, the NPs had approximately 180-200 times increased avidity to the integrins when compared to the monomeric ligand. This result demonstrates that a robust interaction occurs between the NP surface and the surface of the cell. This interaction is independent of surface charge on the NPs and is directly related to a specific receptor ligand interaction an increase of approximately two orders in magnitude of avidity can be achieved by multivalent presentation of a integrin antagonist on the surface of the NPs compared to the free ligand. When the amount of compound 12 in the NP formulations was decreased by 10 fold and 100 fold to 1 mol % and 0.1 mol % as in NP2 and NP3 respectively, the capacity to block cell adhesion decreased by approximately one and two orders of magnitude, respectively as shown in Table 2, below.

TABLE 2

| | Physical and Biological Properties of Liposomes NP1–NP6 | | | |
|---|---|---|---|---|
| Material | Size (nm) | Zeta Potential (mV) | Competitive inhibition Assay (µM of 10) | Cell Adhesion Assay $IC_{50}$ (µM of 10 on NPs) | Effect of Multivalency $IC_{50}$ (Free [10]/[10] on NPs) |
| NP1 | 45.1 ± 0.6 | −42 | 65 | 0.27 | 237 |
| NP2 | 42.8 ± 1.5 | −49 | 24 | 7 | 9 |
| NP3 | 44.4 ± 0.8 | −53 | 1 | 30.5 | 2 |

TABLE 2-continued

Physical and Biological Properties of Liposomes NP1–NP6

| Material | Size (nm) | Zeta Potential (mV) | Competitive inhibition Assay (μM of 10) | Cell Adhesion Assay IC$_{50}$ (μM of 10 on NPs) | Effect of Multivalency IC$_{50}$ (Free [10]/[10] on NPs) |
|---|---|---|---|---|---|
| NP4 | 46.4 ± 0.7 | −49 | NA | No Inhibition | NA |
| NP5 | 41.7 ± 2.2 | 35 | 60 | 0.35 | 183 |
| NP6 | 36.8 ± 0.9 | 43 | NA | No Inhibition | NA |

Liposome NP5 represents an exemplary crosslinked targeting liposome of the present invention.

General Synthetic Methods.

All solvents and reagents used were of reagent grade. Solvent evaporations were performed under reduced pressure provided from house vacuum or a Welch direct drive vacuum pump at ≦40° C. $^1$H and $^{13}$C-NMR spectra were recorded on a JEOL FX90Q at 90 MHz for the proton spectra and at about 23 MHZ for the carbon spectra in CDCl$_3$, CD$_3$OD, D$_2$O or blends thereof as described for each case. (Note: although soluble in CDCl$_3$, the addition of CD$_3$OD to the lipids inhibits formation of inverted micelles and thus provided sharper spectra.) Spectra were referenced to residual CHCl$_3$ (7.25 ppm) for $^1$H experiments and the center line of CDCl$_3$ (77.00 ppm) for $^{13}$C experiments. MALDI-TOF mass spectrometry was performed on PerSeptive DE instrument (Mass Spectrometry, The Scripps Research Institute, La Jolla, Calif.). TLC was performed on glass backed Merck 60 F254 (0.2 mm; EM Separations, Wakefield, R.I.) and the developed plates routinely sprayed with ceric sulfate (1%) and ammonium molybdate (2.5%) in 10% aqueous sulfuric acid and heated to about 150° C. Other developers include iodine (general use), 0.5% ninhydrin in acetone (for amines), and ultraviolet light (for UV chromophores).

N-Benzyloxycarbonyl-taurine sodium salt (2). Taurine, 1 (about 40 g, 320 mmols), was dissolved in 4N sodium hydroxide solution (80 mL) and water (about 200 mL). To this solution was added benzyloxycarbonyl chloride, (about 48 mL, 330 mmols) dropwise, with vigorous stirring during a period of about 4 hours. The pH of the solution was maintained alkaline by the addition of 10% sodium bicarbonate solution (about 300 mL) and 4N sodium hydroxide solution (about 45 mL). The obtained reaction mixture was then washed with diethyl ether (about 1000 mL) and the aqueous layer was rotary evaporated to dryness, and further dried under high vacuum over phosphorous pentoxide overnight to yield about 12.7 g (14%) of 2. $^1$H-NMR (D$_2$O): δ 7.50 (5H, s, Ar—H), 5.21 (2H, s, Ar—CH$_2$), 3.62 (2H, t, CH$_2$), 3.14 (2H, t, CH$_2$).

2-Benzyloxycarbonylamidoethanesulfonyl chloride (3). N-CBZ-taurine sodium salt 2 (about 12.7 g, 32 mmols) was suspended in dry diethyl ether (about 30 mL) under a positive pressure of argon and treated with phosphorous pentachloride (about 7 g, 33.6 mmols) in 5 portions over about 15 minutes. The reaction was stirred for about 4 h, at ambient temperature. The solvent was removed by rotary evaporation. Ice water (about 10 mL) was added and the residue obtained was triturated after cooling the flask and the contents in an ice bath. More ice water (about 50 mL) was added, and the product solidified. The solids were collected by filtration, washed with ice water (about 20 mL), and dried over phosphorous pentoxide overnight to yield about 6.95 g (78%) of 3. $^1$H-NMR (CDCl$_3$): δ 7.35 (5H, s, Ar—H), 5.12 (2H, s, Ar—CH$_2$), 3.89 (2H, t, CH$_2$) overlapping with 3.85 (2H, t, CH$_2$).

Methyl 3-butyloxycarbonylamido-2-(S)-benzyloxycarbonyl-amidoethylsulfonamidopropionate (5). A mixture of the sulfonyl chloride 3 (about 21.6 g, 78 mmols) and methyl-3-N-butoxycarbonylamido-2-aminopropionate (4, about 9.96 g, 39.2 mmols) in anhydrous tetrahydrofuran (THF, 150 mL) under a positive pressure of argon was cooled in an ice bath. To this solution was added N-methylmorpholine (about 16 mL, 145 mmols) in anhydrous THF (about 275 mL) drop wise during a period of about 30 min using a dropping funnel previously dried and under a positive pressure of argon. After about 1 h stirring in the ice bath, it was observed by TLC that substantially all the sulfonyl chloride (R$_f$=0.65) had been consumed (eluent: ethyl acetate/hexane 1:1). However there was unreacted diaminopropionic acid (R$_f$=0.1, ninhydrin spray) still present. More sulfonyl chloride (about 5.0 g, 18 mmols) was added during a period of about 3 h. The obtained reaction product was then filtered and rotary evaporated to remove the solvent and dissolved in ethyl acetate (about 100 mL), washed with cold dilute hydrochloric acid (about 20 mL), saturated sodium bicarbonate solution (about 20 mL), and then saturated sodium chloride solution (about 20 mL), and then dried over anhydrous sodium sulfate. The solvent was removed by rotary evaporation, and the produced residue was dried under vacuum over night. The dried residue was recrystallized by first dissolving in ethyl acetate and then by adding equal volume of hexane to obtain the methyl ester 5 as a colorless solid, about 13.4 g (about 74%). $^1$H-NMR (CDCl$_3$): δ 7.36 (5H, s, Ar—H), 5.83 (1H, d, NH), 5.55 (1H, t, NH), 5.12 (2H, s, Ar—CH$_2$), 5.06 (1H, t, NH), 4.26 (2H, m, CH), 3.79 (3H, s, CH$_3$), 3.70 (2H, dd, CH$_2$), 3.26 (2H, dd, CH$_2$), 1.43 (9H, s, (CH$_3$)$_3$).

3-Butyloxycarbonylamido-2-(S)-benzyloxycarbonylamido-ethylsulfonamidopropionic acid (6). A solution of the methyl ester 5 (about 13.3 g, 28.9 mmols) in tetrahydrofuran (about 160 mL) was cooled in an ice bath. To this solution was added a solution of lithium hydroxide (about 5.42 g, 128 mmols) in ice water (160 mL). The produced reaction mixture was slowly warmed to ambient temperature by removing the ice bath and the mixture was stirred at ambient room temperature for about 1 h. The organic solvent was then removed by rotary evaporation. The residual aqueous portion was washed with diethyl ether (about 20 mL) and then acidified to about pH 4 using diluted hydrochloric acid. This solution was cooled in an ice bath, then mixed with ethyl acetate (about 100 mL), and then further acidified to about pH 1 using ice-cold diluted hydrochloric acid and immediately extracted with ethyl acetate (about 2×200 mL). The ethyl acetate layer was washed with brine (about 50 mL) and dried over anhydrous sodium sulfate. The solvent was then removed by rotary evaporation, and the obtained residue was dried under high vacuum over night to obtain about 13.3 g of a foamy solid, which was recrystallized from hexane/ethyl acetate (1:1) to obtain about 11.6 g (89.7%) of 6. $^1$H-NMR (CDCl$_3$): δ 7.33 (5H, s, Ar—H), 6.12 (1H, d, NH), 5.68 (1H, t, NH), 5.26 (1H, t, NH), 5.1 (2H, s, Ar—CH$_2$), 4.24 (2H, m, CH$_2$), 3.67 (2H, t, CH$_2$), 3.27 (2H, t, CH$_2$), 1.45 (9H, s, C(CH$_3$)$_3$).

3-Amino-2-(S)-benzyloxycarbonylamidoethyl-sulfonamido-propionic acid (7). N—BOC-β-amino acid 6 (about 11.5 g, 25.8 mmols) was treated with trifluoroacetic acid (about 68 mL) in methylene chloride (about 350 mL) for about 1.5 h and then rotary evaporated to dryness. The obtained residue was dissolved in water (about 200 mL) and lyophilized to obtain about 10.9 g (98.8%) of 7 as a solid. $^1$H-NMR (CDCl$_3$): δ 7.30 (5H, s, Ar—H), 6.07 (1H, d, NH), 5.61 (1H, t, NH), 5.20 (1H, t, NH), 5.17 (2H, s, Ar—CH$_2$), 4.11 (2H, m, CH$_2$), 3.53 (2H, t, CH$_2$), 3.32 (2H, t, CH$_2$). DCI-MS for C$_{13}$H$_{19}$N$_3$O$_6$S: m/z (ion) 346 (M+H) (calcd for C$_{13}$H$_{19}$N$_3$O$_6$S+H, m/z 346).

4-[2-(Pyrimidin-2-ylamino)ethyloxy]benzoyl-2-(S)-benzyloxycarbonylamidoethylsulfonamido-β-alanine (9). The benzoic acid derivative 8 (about 6.4 g, 24.7 mmols) and N-hydroxysuccinimide (about 3.6 g, 31 mmols) were dissolved in anhydrous dimethylsulfoxide (about 110 mL), under a positive pressure of argon, and cooled in an ice bath. To this solution was added 1-(3-(dimethylamino)propyl)-3-ethylcarbodiimide hydrochloride (about 4.9 g, 25.6 mmols). The solution was stirred at ice-cold temperature for 1 h and then allowed to warm to ambient room temperature. Stirring was continued at room temperature for about another 24 h. To the produced mixture was added a solution of the β-amino acid 7 (about 12.2 g, 25.8 mmols) followed by N-methylmorpholine. The produced reaction mixture was stirred under argon for about 3 days. The resulting mixture was then poured into water (about 1 L), acidified with diluted hydrochloric acid to about pH 1.5, and extracted with ethyl acetate (about 5×500 mL). The combined organic phase was washed with saturated sodium chloride solution (about 50 mL) and then dried over anhydrous sodium sulfate. The solvent was removed by rotary evaporation. The obtained residue was triturated in ethyl acetate, filtered, and then dried under high vacuum to obtain about 10.5 g (72.5%) of 9. $^1$H-NMR (DMSO-d$_6$): δ 8.30 (2H, d, Ar—H), 7.99 (2H, d, Ar—H), 7.34 (5H, s, Ar—H), 7.00 (2H, d, Ar—H), 6.60 (1H, dd, Ar—H), 5.01 (2H, s, CH$_2$), 4.15 (1H, t, CH), 3.67 (2H, t, CH$_2$), 3.56 (2H, t, CH$_2$), 3.17 (2H, t, CH$_2$).

4-[2-(3,4,5,6-Tetrahydropyrimidin-2-ylamino)ethyloxy]benzoyl-2-(S)-aminoethylsulfonamido-β-alanine (10). A solution of the pyrimidine derivative 9 (about 3.7 g, 6.4 mmols) was dissolved in acetic acid (about 190 mL) and concentrated hydrochloric acid (about 17 mL). The obtained solution was mixed with 10% palladium over carbon (about 1.62 g) and hydrogenated at about 45 psi of hydrogen gas for about 5 h. The produced mixture was then filtered through celite and washed with water. The solvent was removed by rotary evaporation, and the obtained residue was dried under high vacuum. The dried residue was dissolved in water (about 100 mL), pH adjusted to about 7 with 1N sodium hydroxide solution, and then rotary evaporated to dryness. The obtained residue was dissolved in methanol (about 20 mL) and filtered. The filtrate was rotary evaporated, dissolved in water (about 275 mL) and lyophilized. The obtained lyophilized product was then recrystallized from water to obtain about 2.96 g (about 78.9%) of product 10. $^1$H-NMR (D$_2$O): δ 7.80 (2H, d, Ar—H), 7.14 (2H, d, Ar—H), 4.49 (1H, s, CH$_a$H$_b$), 4.28 (2H, t, CH$_2$), 3.94 (1H, dd, CH$_a$H$_b$), 3.61 (6H, m, CH$_2$), 3.32 (4H, t, CH$_2$), 1.90 (2H, t, CH$_2$). ES-MS for C$_{18}$H$_{28}$N$_6$O$_6$S: m/z (ion) 457 (M+H) (calcd for C$_{18}$H$_{28}$N$_6$O$_6$S+H, m/z 457).

[(PDA-PEG3)$_2$-DTPA-(CONHPM)$_3$] (12). (PDA-PEG3)$_2$-DTPA-(COOH)$_3$ (about 11, 69 mg, 50 μmole) was dissolved in anhydrous CH$_3$CN (about 5 mL), anhydrous CH$_2$Cl$_2$ (about 2 mL) and Et$_3$N (about 1 mL) in a 3-neck RB flask, previously flame dried and filled with argon. To the resulting solution was added the BOP reagent (about 134 mg 150 μmole), and the produced admixture stirred well for 5 minutes to obtain a lipid solution. A solution of 10 (about 69 mg, 150 μmole) was prepared in a dry vial filled with argon, in a mixture of anhydrous CH$_3$CN (about 5 mL) and anhydrous dimethylformamide (DMF) (about 2 mL). The solution of 10 was added to the lipid solution using a dry syringe with continuous stirring. The reaction mixture so produced was stirred for 10 hours in dark. TLC (solvent: CHCl$_3$, CH$_3$OH, H$_2$O, and CH$_3$COOH showed complete disappearance of the starting material (R$_f$=0.53). There was one major product (R$_f$=0.2) and 5 minor products (R$_f$<0.18). The solvent was removed by rotary evaporation, and the obtained residue was dried under high vacuum for about 24 hours to obtain a crude product. The crude product was purified by normal phase HPLC using a semi preparative silica column, flow rate about 5 mL/min (gradient system starting with 100% CHCl$_3$ for about 5 minutes, then 75% CHCl$_3$/25% CH$_3$OH for 10 minutes, then 50% CHCl$_3$/50% CH$_3$OH for 10 minutes, then 25% CHCl$_3$/75% CH$_3$OH for about 10 minutes, and finally for about 20 minutes with 100% CH$_3$OH). The fractions (retention time=35 to 37 minutes) that contained the major product were combined and rotary evaporated to remove the solvent, and the obtained residue was dried under high vacuum for about 24 hours to obtain about 35.5 mg (26.5%) of the desired product. High resolution MALDI-FTMS: m/z 2681.4711 (calcd for C$_{130}$H$_{209}$N$_{25}$O$_{29}$S$_3$+H, m/z 2681.4882).

EXAMPLES

Example 1

Cell Adhesion Assay

Cell adhesion inhibition study was done on plates coated with vitronectin using human melonoma cell line M21. The multivalent liposomes NP1-NP6 as well as the monomeric ligand 10 were separately incubated with M21 cells and applied onto the 48 well plates coated with vitronectin. After about 1 hour incubation, the wells were washed, and the cells that adhered were stained with a solution of crystal violet and the optical density (OD) at about 590 nm was measured. The OD measured was proportional to the number of cells bound to the vitronectin plate and was plotted against the concentration of component 10 on the surface of the NPs in different formulations to calculate the IC50.

Figure 8:
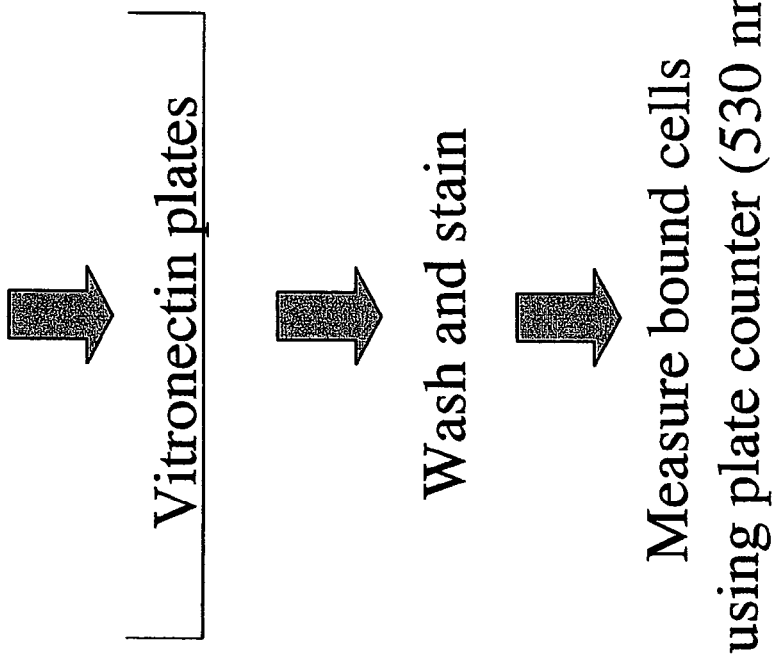
FIG. 8 schematically illustrates an adhesion assay suitable for the testing of $\alpha_v\beta_3$ antagonists.

FIG. 8 schematically depicts the cell adhesion assay wherein M21 human melanoma cells, which express α$_v$β$_3$, were mixed with liposomes covalently conjugated to an integrin antagonist (ligand) or to ligand alone. The cells were then placed on vitronectin plates, washed and stained. The number of bound cells was then counted using a plate counter.

Figure 9:
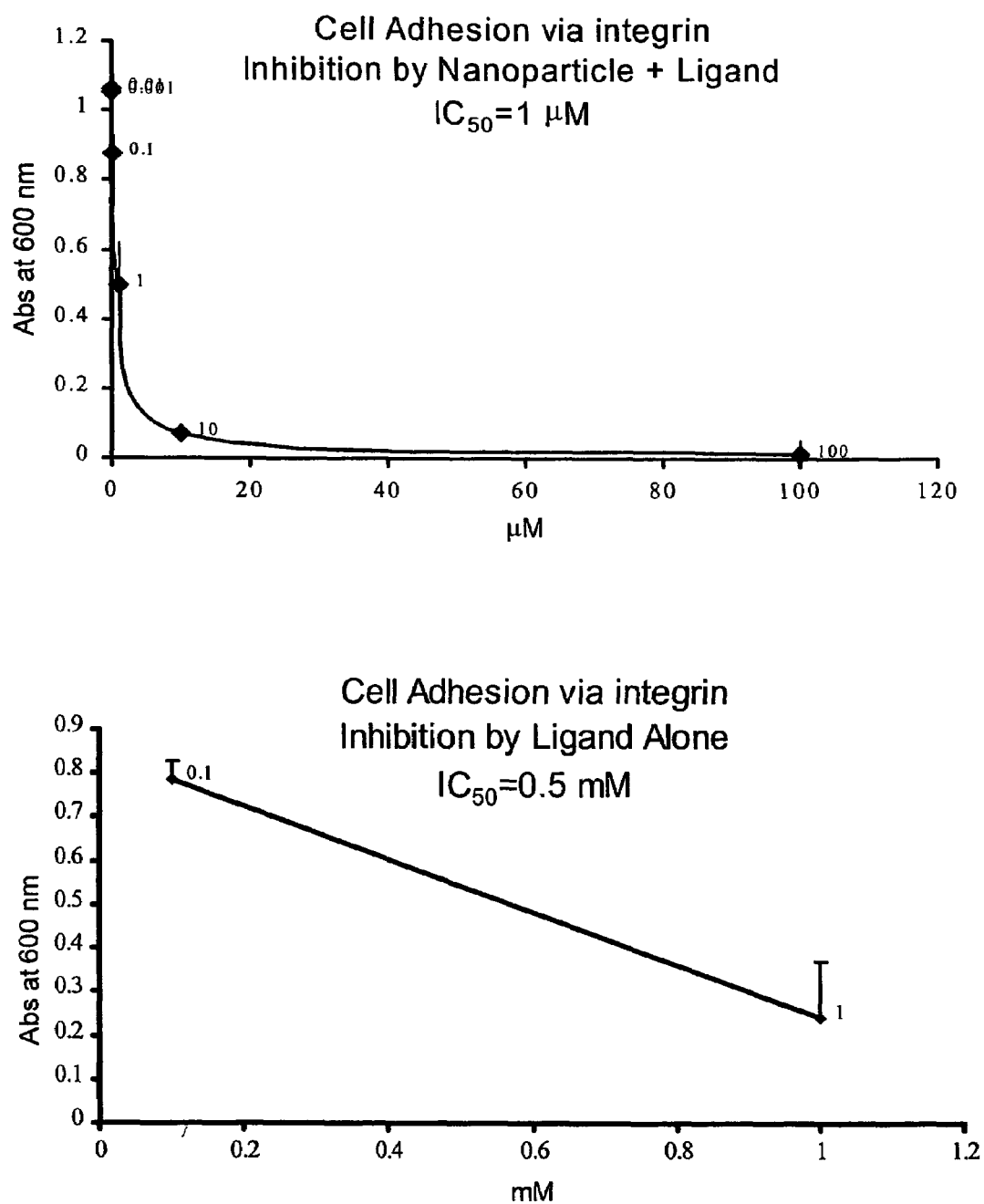
FIG. 9 is a graphical presentation of data obtained utilizing the adhesion assay shown in FIG. 8 and showing that a targeting liposome of the present invention binds to an $\alpha_v\beta_3$ receptor.

FIG. 9 is a graphical presentation of data obtained utilizing the adhesion assay shown in FIG. 8 and showing that the liposomes bound to integrin antagonist strongly inhibit cell adhesion (IC50=1 μM), whereas the antagonist alone (ligand) was much less effective at inhibiting cell adhesion (IC50=0.5 mM).

Example 2

In Vitro Transfection Assay

About thirty nanomoles of cationic liposomes NP5 and NP6, with or without covalently conjugated α$_v$β$_3$-targeting ligand, respectively, were each complexed to about 2 μg of plasmid DNA encoding green fluorescent protein (GFP) in 5% dextrose and then exposed to melanoma cells in vitro for about 1 hour. Transfection efficiency was assayed by counting the number of fluorescent cells as compared to total cell number after 24 hours. The cells used were human melanoma cells M21 and M21L. M21 cells express $\alpha_v\beta_3$ integrin while M21L cells do not express $\alpha_v\beta_3$ integrin ($\alpha_v$-null).

Figure 10:
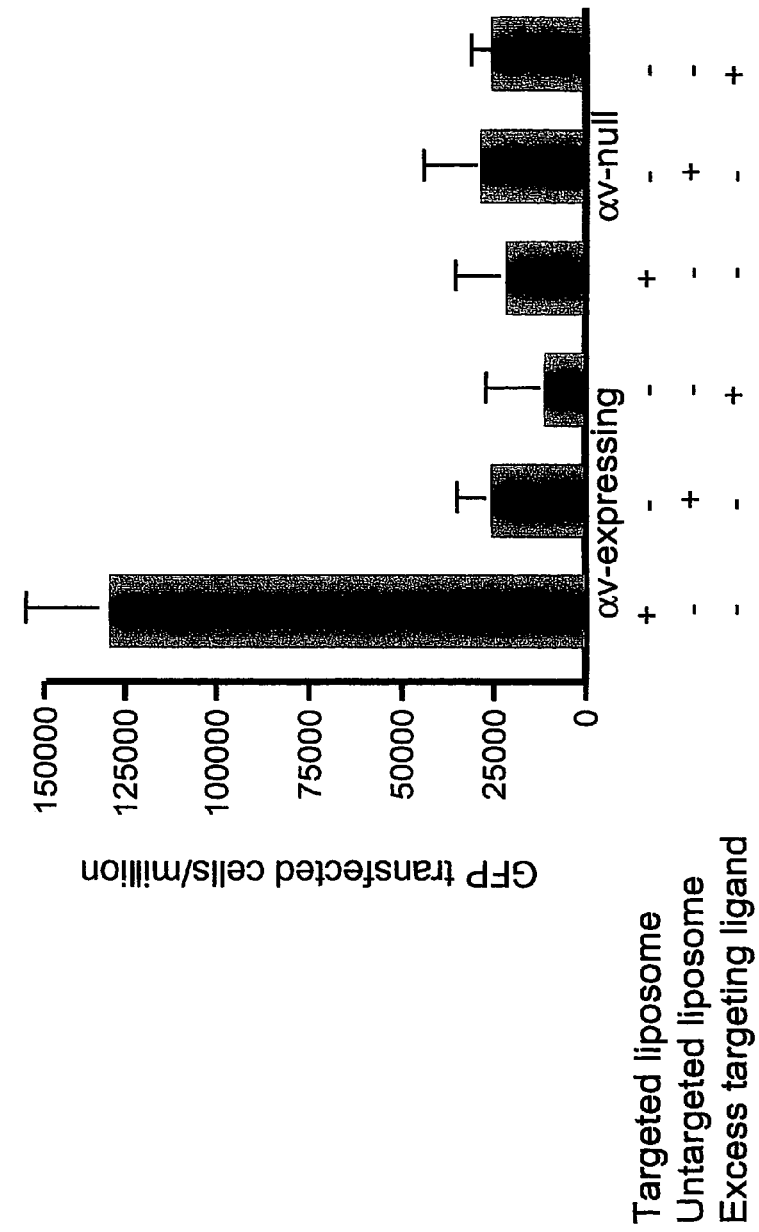
FIG. 10 is a graphical presentation of data showing effective green fluorescing protein (GFP) gene delivery targeted to $\alpha_v\beta_3$ expressing cells in vivo utilizing a targeting liposome of the invention; the targeting liposome carrying the gene are shown to transfect cells in an $\alpha_v\beta_3$ dependent manner; the cells used were human melanoma cells M21 and M21L; M21 cells express $\alpha_v\beta_3$ integrin while M21L cells do not express $\alpha_v\beta_3$ integrin ($\alpha_v$-null)

As shown in FIG. 10, the $\alpha_v$ expressing cells (M21) that were treated with the targeted liposome (NP5) complexed with the GFP gene exhibited a 5-fold or greater degree of transfection (>125,000 cells/million) compared to $\alpha_v$-expressing cells that were treated with non-targeted liposomes (NP6) (no antagonist; about 25,000 cells/million) or DNA alone (no liposome, about 12,000 cells/million). In contrast, the $\alpha_v$-null cells (M21L) exhibited no preferential incorporation of the GFP gene, affording relatively low levels of transfection (25,000 cells/million, or less) regardless of the treatment received. Thus, the targeted gene carriers are shown to transfect cells in an $\alpha_v\beta_3$ dependent manner.

Example 3

Targeting Liposome-Mediated Gene Delivery is Targeted to the Tumor In Vivo

About 450 nanomoles each of NP5 and NP6, were electrostatically complexed to about 30 μgs each of plasmid DNA encoding firefly luciferase in about 200 μls each of 5% dextrose and then each liposome complexed DNA solution was intravenously injected into animals bearing about 150 mm³ subcutaneous melanomas lacking $\alpha_v\beta_3$ expression (M21L). After about 24 hours the animals were sacrificed, the described organs and tumors were excised, and assayed for luciferase activity. Luciferase activity was assayed using the Bright-Glo luciferase assay kit (Promega Corp., Madison, Wis.) according to manufacturer's directions with the exception that whole organs were ground using a tissue grinder in an amount of Bright-Glo lysis reagent normalized to weight of the organ.

Figure 11:
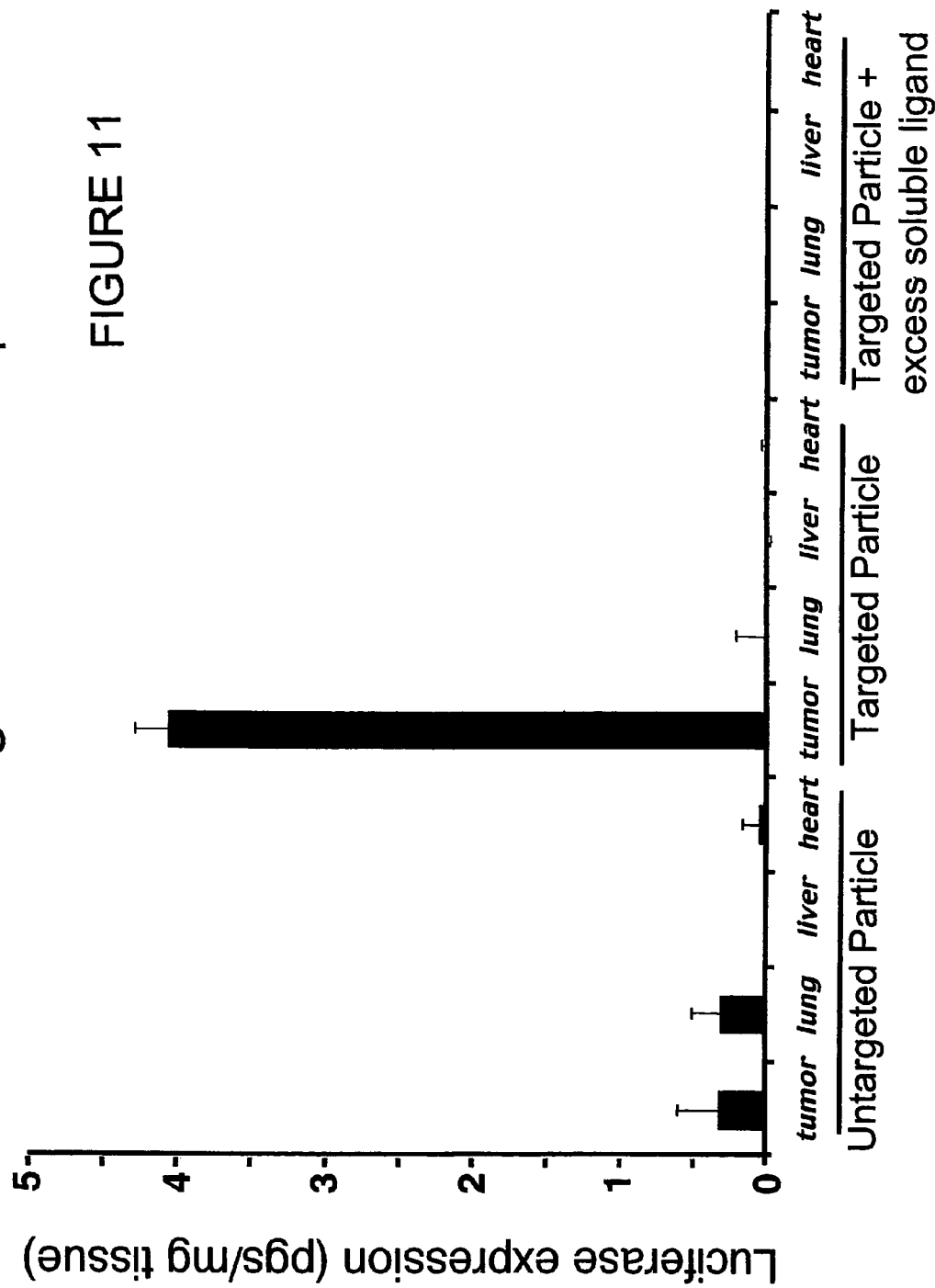
FIG. 11 is a graphical presentation of data demonstrating selective in vivo targeting of firefly luciferase gene to $\alpha_v\beta_3$ expressing tumor vasculature cells utilizing a targeting liposome of the invention; the targeted gene carriers are shown to transfect tumor cells in an $\alpha_v\beta_3$ dependent manner; the cells used were human melanoma cells M21 and M21L, implanted in mice; M21 cells express $\alpha_v\beta_3$ integrin while M21L cells do not express $\alpha_v\beta_3$ integrin.

As shown in FIG. 11, the targeted liposome (NP5), complexed with luciferase gene, exhibited a highly selective expression in the tumor tissue relative to the lung, liver and heart tissues, having an expression level of about 4 picograms of luciferase/mg tissue compared to sub-picogram/mg tissue levels in the other tissues evaluated. The untargeted liposome (NP6), complexed with the luciferase, was ineffective at transfecting any of the tissues. Addition of about 20-fold excess of soluble integrin antagonist ligand effectively inhibited transfection of the cells by the targeted ligand.

Example 4

Targeting Liposome-Mediated Delivery of Mutant Raf Genes to the Tumor Vasculature Regresses Established Melanomas Melanomas lacking $\alpha_v\beta_3$ expression (M21L) were injected subcutaneously on the flank and allowed to grow to about 70 mm³, at which point the mice were intravenously injected with either 200 μL of 5% dextrose (control), targeted liposome NP5 and complexed to either about 30 μg of plasmid DNA encoding a mutant dominant negative form of Raf kinase (Raf-ATP$^\mu$) in 200 μls of 5% dextrose, or complexed to a shuttle vector not encoding any DNA in 200 μL of 5% dextrose. About fifteen days later, tumors were again injected with the same treatments. Tumor size was measured at the time points indicated in FIG. 12 using the formula: tumor volume=(minimum diameter)²*maximum diameter/2.

Figure 12:
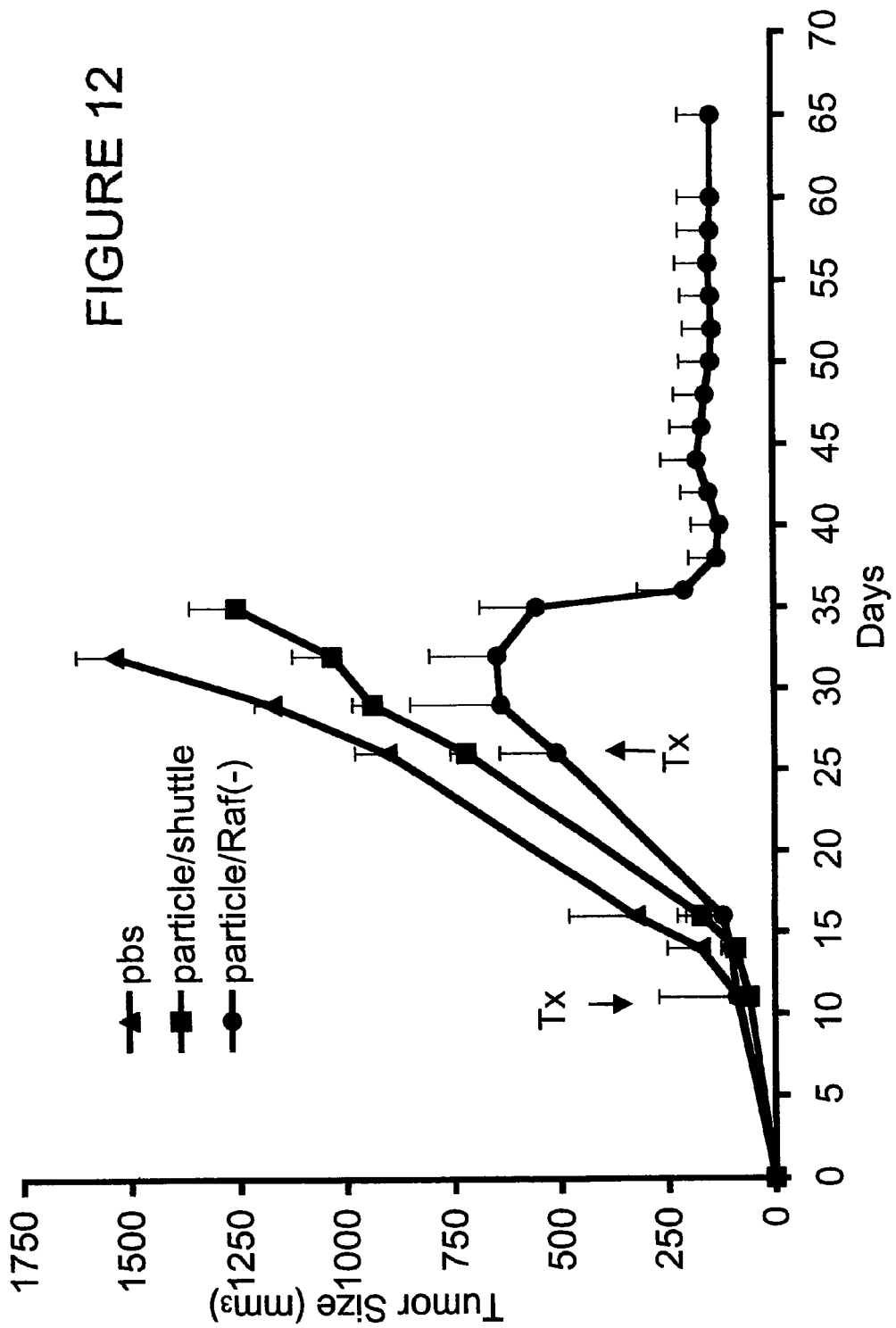
FIG. 12 is a graphical presentation of data demonstrating in vivo inhibition and regression of tumor growth in established tumors due to administration of a targeting liposome bound to gene expressing an angiogenesis-inhibiting mutant Raf protein.

As shown in FIG. 12, treatment of mice bearing melanoma tumors of about 70 mm³ initial volume with the targeting liposome NP5 complexed with mutant dominant negative form of Raf kinase (Raf-ATP$^\mu$), led to an initial increase in tumor volume to about 550 mm³, followed by a regression of the tumors after about 30 days, which leveled off to a steady state of about 200 mm³ volume by day 35 (labeled "particle/Raf(−)" in FIG. 12). This steady state tumor size was maintained for an additional 30 days, at which time the experiment was terminated. In mice treated with targeting liposome NP5 (no gene) alone (labeled "Particle/shuttle"), or the mutant Raf gene alone (no liposome), the tumors continued to grow over the entire period of 35 days, with no indication of any regression. Inasmuch as the tumors lack $\alpha_v\beta_3$ expression, but the neovascular endothelial cells do express $\alpha_v\beta_3$, the reduction in tumor growth was most likely due to inhibition of angiogenesis in the tumor vasculature.

Example 5

Targeting Liposome-Mediated Delivery of Mutant Raf Genes to the Tumor Vasculature Regresses Established Melanomas Tumors were treated as in Example 4, except that tumors were allowed to grow to about 300 mm³ before initial treatment, at which point they were injected with either (a) about 450 nanomoles of targeting liposome NP5 and electrostatically complexed to about 30 μg of plasmid DNA encoding Raf-ATP$^\mu$ in about 200 μL of 5% dextrose, (b) about 450 nanomoles of untargeted liposome NP6 electrostatically complexed to about 30 μgs of plasmid DNA encoding Raf-ATP$^\mu$ in 200 μL of 5% dextrose, or (c) about 450 nanomoles targeting liposome NP electrostatically complexed to about 30 μg of plasmid DNA encoding Raf-ATP$^\mu$ mixed with a about 20 molar excess of a competing ligand for integrin $\alpha_v\beta_3$ in about 200 μL of 5% dextrose. Tumor measurements were taken at the time points indicated in FIG. 13, where (a) is labeled "Raf (−)", (b) is labeled "untargeted", (c) is labeled "excess". A control with no treatment was also included.

Figure 13:
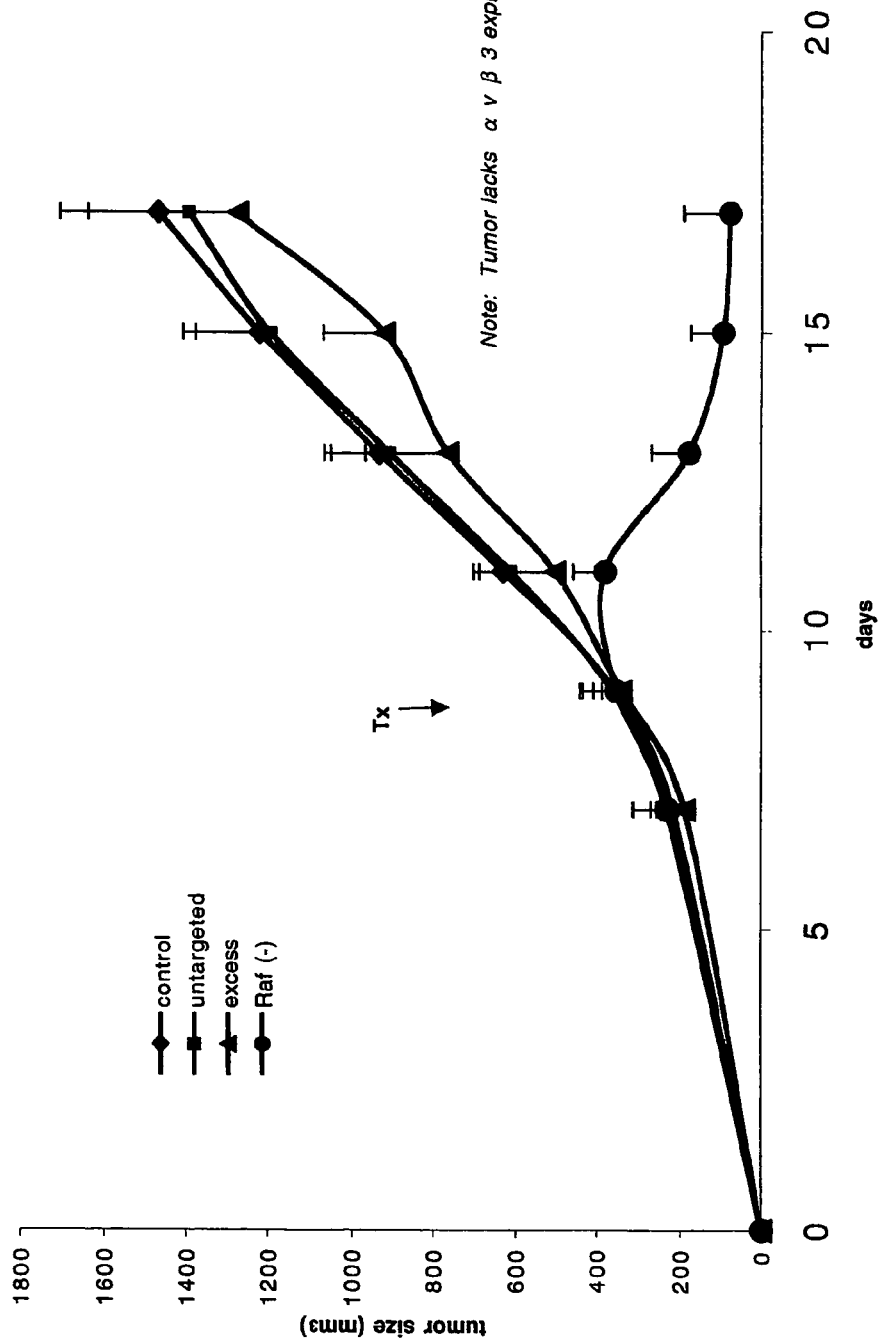
FIG. 13 is a graphical presentation of data demonstrating in vivo inhibition and regression of tumor growth in established tumors due to administration of a targeting liposome bound to gene expressing an angiogenesis-inhibiting mutant Raf protein.

As shown in FIG. 13, treatment of mice, bearing melanoma tumors of 300 mm³ initial volume, with the targeting liposome NP5 complexed with mutant dominant negative form of Raf kinase (Raf-ATP$^\mu$), after an initial growth period also led to a regression of the tumor volume compared to a control groups with no treatment.

Example 6

Targeting Liposome-Mediated Delivery is Selective for Angiogenic Vessels

About 300 nanomoles of NP5 was complexed to about 20 μg of plasmid DNA encoding green fluorescent protein (GFP) in about 50 μL of 5% dextrose and then intravenously injected into chick embryos whose chorioallantoic membrane (CAM) had previously been exposed to a filter disk saturated with 1 mg/ml bFGF for about 24 hours to stimulate angiogenesis. One day after complex injection, CAM tissue was harvested, washed with PBS, fixed in 4% paraformaldehyde and examined for the presence of fluorescence. The results are presented in FIG. 14.

Figure 14:
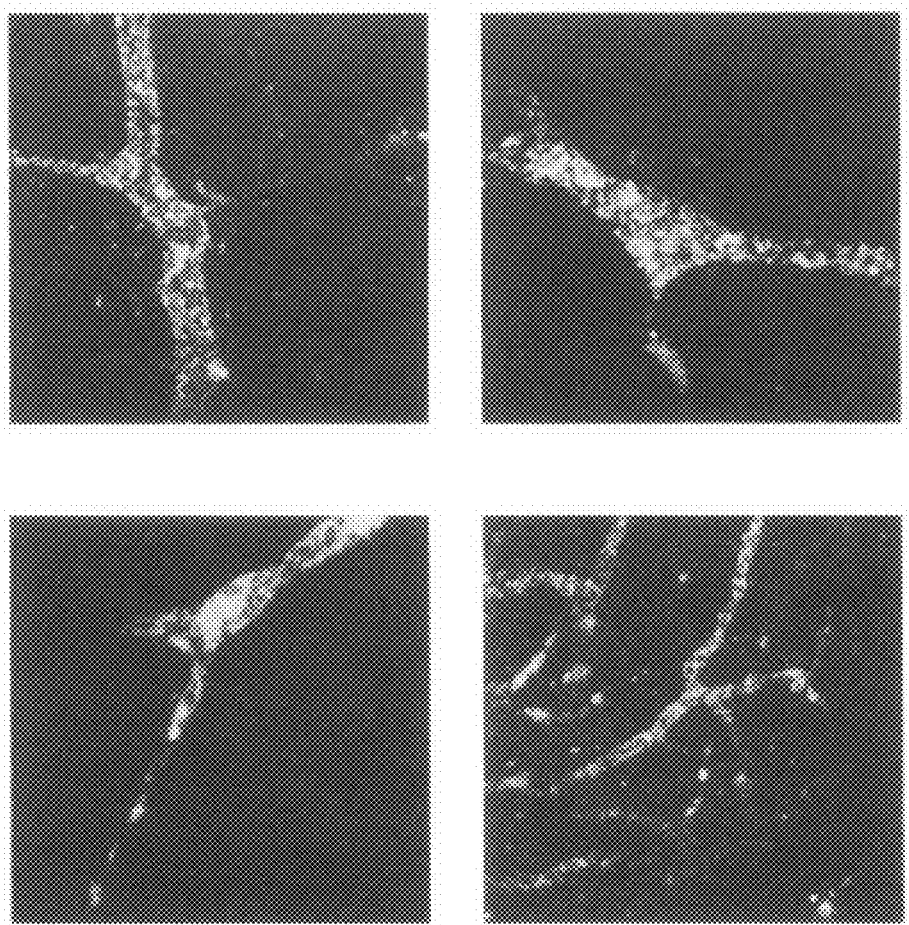
FIG. 14 depicts photomicrographs demonstrating in vivo delivery of a gene encoding GFP to angiogenic blood vessels in a chick CAM utilizing a targeting liposome of the invention.

GFP was highly localized in the vasculature of the CAMs as can be seen from the photomicrographs in FIG. 14.

Example 7

Targeting Liposome-Mediated Delivery of Mutant Raf Genes to the Tumor Vasculature Induces Vasculature Apoptosis and Subsequent Tumor Cell Death Melanomas lacking $\alpha_v\beta_3$ expression were injected subcutaneously on the flanks of mice. The resulting tumors were allowed to grow to about 200 mm³, at which point the mice were intravenously injected with about 450 nanomoles of NP5 and complexed to either about 30 μg of plasmid DNA encoding Raf-ATP$^\mu$ or a shuttle vector in about 200 μL of 5% dextrose. Tumors were excised after about 72 hours, fixed in 4% paraformaldehyde, sectioned, and stained for von Willebrand factor (a vessel marker) and apoptosis using the TUNEL method for detecting fragmented DNA (Intergen Corp, Purchase, N.Y.).

The photomicrographs shown in FIG. 15 indicate that tumors exposed to the nanoparticle/shuttle vector (control) showed a relatively high density of vessels with few cells undergoing apoptosis. In contrast, the majority of vessels in tumors exposed to NP5/Raf-ATP$^\mu$ were undergoing apoptosis and large regions of tumor were dying at fixed distances from the apoptosing vessels, presumptively due to insufficient perfusion.

Example 8

Targeting Liposome-Mediated Delivery is Selective for Angiogenic Vessels

In the mouse, collateral branches sprout from retinal capillaries of the superficial plexus, penetrating into the retina and forming a deep vascular plexus between postnatal days 8 (P8) and 10 (P10). In this study, mice were injected at P10 intravitreally with targeting liposome NP5 complexed to about 0.15 μg of plasmid DNA encoding green fluorescent protein in about 1 μL of 5% dextrose and then intravitreally injected. About 24 hours after injection of NP5 complexed with GFP gene, mice were sacrificed and retinas immunostained with rhodamine linked anti-collagen IV antibodies (a vascular marker) and evaluated by 2-photon laser scanning microscopy to detect the relative level of GFP in the retinal blood vessels.

Figure 16:
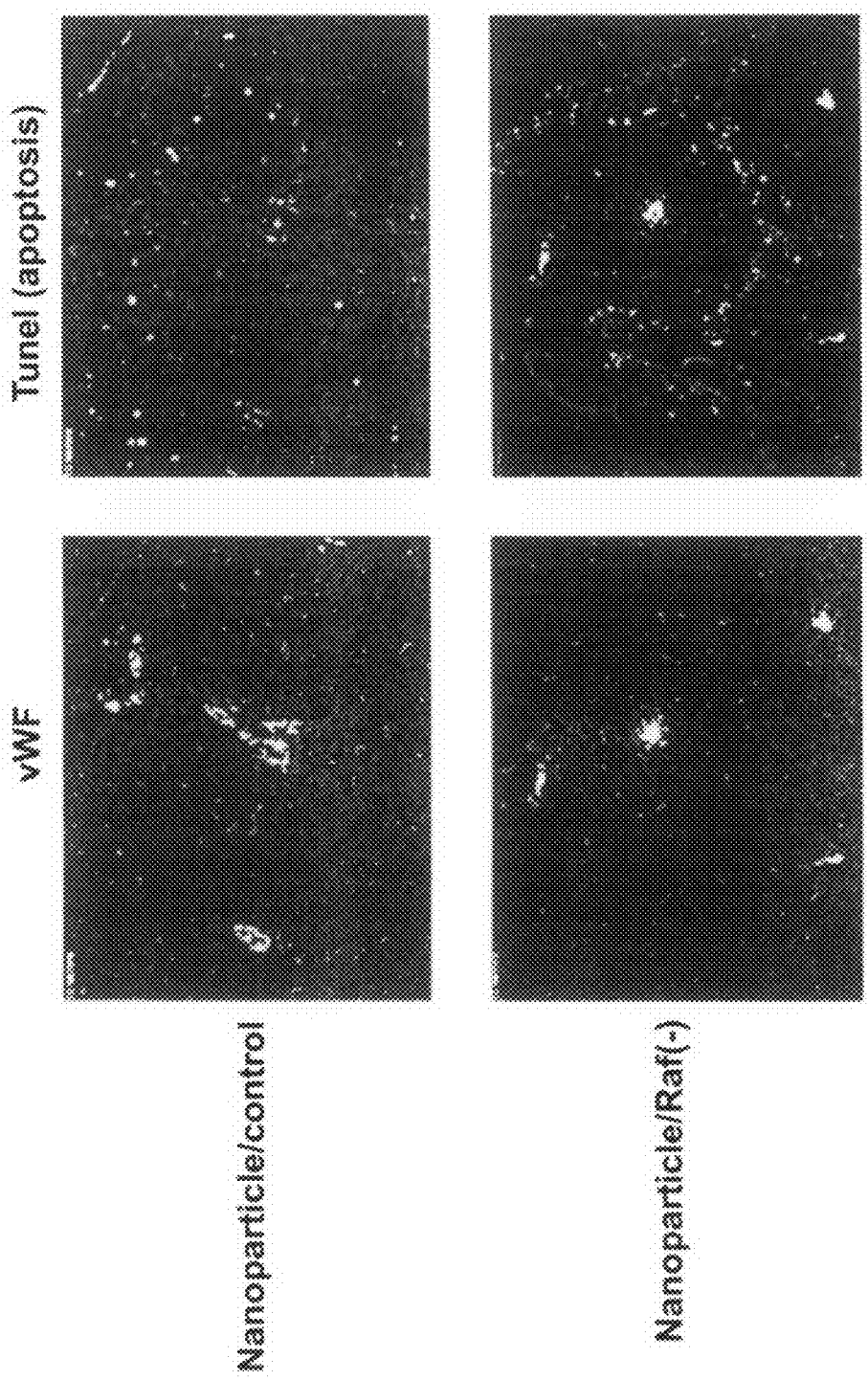
FIG. 16 depicts photomicrographs demonstrating in vivo neovascular apoptosis by targeting liposome mediated delivery of a gene encoding mutant Raf to angiogenic blood vessels in mouse retinas.

The photomicrographs in FIG. 16 show that GFP was highly localized in the retinal vasculature.

Numerous variations and modifications of the embodiments and examples described above may be effected without departing from the spirit and scope of the novel features of the invention. No limitations with respect to the specific embodiments illustrated herein are intended or should be inferred. The appended claims are intended to cover all such modifications as fall within the scope of the claims.

We claim:

1. An $\alpha_v\beta_3$ integrin receptor targeting liposome comprising a cationic lipid;
a neutral lipid;
a trivalent targeting lipid having a targeting domain and a hydrophobic domain bound to the targeting domain; and
a nucleic acid complexed with the cationic lipid;
the cationic lipid being present in an amount in the range of about 1 to about 50 mole percent, and said targeting lipid being present in an amount in the range of about 1 to about 20 mole percent, the mole percent values being based on total moles of lipid in the liposome, and the targeting domain including three non-peptidic $\alpha_v\beta_3$ integrin antagonists represented by formula (II):

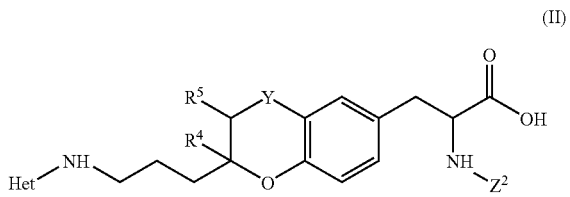

(II)

wherein in formula (II), $R^4$ and $R^5$ are each hydrogen, or together form a covalent bond; Y is —C(O)— or —CH$_2$—; $Z^2$ is —C(O)—$R^6$; —C(O)OR$^6$, or SO$_2$R$^6$; $R^6$ is phenyl, substituted-phenyl, pyridyl, benzyl, substituted-benzyl; $C_1$-$C_4$ haloalkyl, $C_2$-$C_{30}$ alkyl, $C_2$-$C_{30}$ alkenyl, $C_2$-$C_{30}$ alkynyl, or cholesteryl; and Het is 2-pyridyl or 2-imidazolyl.

2. The liposome according to claim 1 wherein the $\alpha_v\beta_3$ integrin antagonist has the formula

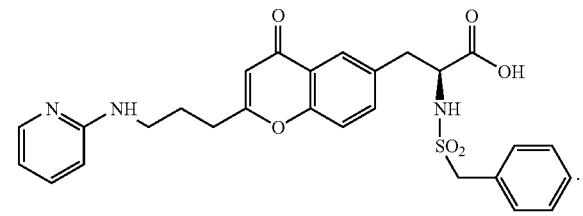

3. The liposome according to claim 1 wherein the $\alpha_v\beta_3$ integrin antagonist has the formula

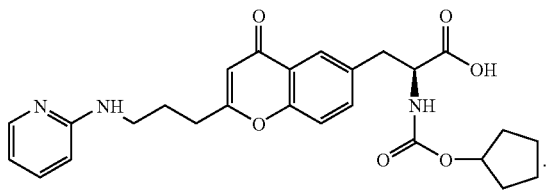

4. The liposome according to claim 1 wherein the $\alpha_v\beta_3$ integrin antagonist has the formula

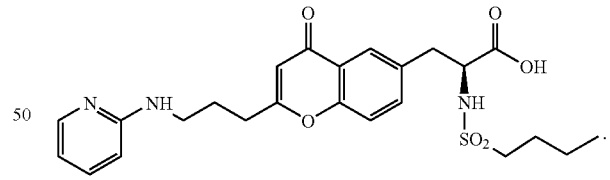

5. The liposome according to claim 1 wherein the $\alpha_v\beta_3$ integrin antagonist has the formula

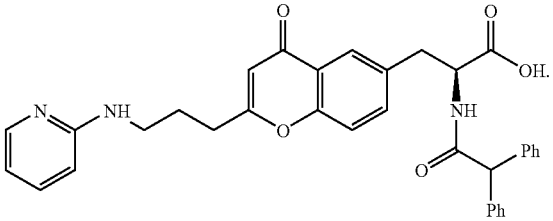

6. The liposome according to claim 1 wherein the $\alpha_v\beta_3$ integrin antagonist has the formula

7. The liposome according to claim 1 wherein the α$_v$β$_3$ integrin antagonist has the formula
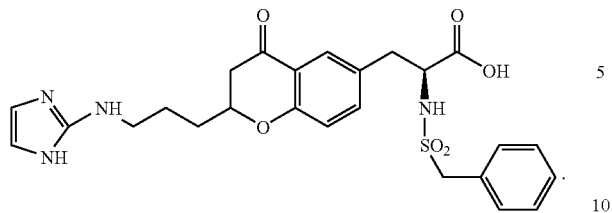
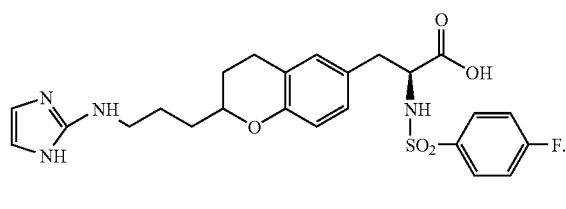
* * * * *